(12) United States Patent
Kaplitt et al.

(10) Patent No.: US 8,067,156 B2
(45) Date of Patent: Nov. 29, 2011

(54) METHOD FOR GENERATING REPLICATION DEFECTIVE VIRAL VECTORS THAT ARE HELPER FREE

(75) Inventors: Michael G. Kaplitt, New York, NY (US); Sergei Moussatov, New York, NY (US)

(73) Assignee: The Rockefeller University, New York, NY (US)

( * ) Notice: Subject to any disclaimer, the term of this patent is extended or adjusted under 35 U.S.C. 154(b) by 244 days.

(21) Appl. No.: 10/159,968

(22) Filed: May 31, 2002

(65) Prior Publication Data

US 2003/0152914 A1 Aug. 14, 2003

Related U.S. Application Data

(60) Provisional application No. 60/294,797, filed on May 31, 2001, provisional application No. 60/313,007, filed on Aug. 17, 2001.

(51) Int. Cl.

| | | |
|---|---|---|
| *C12Q 1/70* | (2006.01) | |
| *C12Q 1/68* | (2006.01) | |
| *C12N 7/00* | (2006.01) | |
| *C12N 15/861* | (2006.01) | |
| *A01N 43/04* | (2006.01) | |
| *A61K 31/70* | (2006.01) | |

(52) U.S. Cl. ............. 435/5; 435/6; 435/456; 435/235.1; 435/320.1; 514/44

(58) Field of Classification Search .......................... None
See application file for complete search history.

(56) References Cited

U.S. PATENT DOCUMENTS

| | | | |
|---|---|---|---|
| 5,478,745 A * | 12/1995 | Samulski et al. | 435/320.1 |
| 5,658,724 A | 8/1997 | DeLuca | |
| 5,869,305 A | 2/1999 | Samulski et al. | |
| 6,221,646 B1 * | 4/2001 | Dwarki et al. | 435/235.1 |
| 6,261,834 B1 | 7/2001 | Srivastava | |
| 6,436,392 B1 * | 8/2002 | Engelhardt et al. | 424/93.2 |
| 6,491,907 B1 * | 12/2002 | Rabinowitz et al. | 424/93.2 |
| 6,893,865 B1 * | 5/2005 | Lockert et al. | 435/320.1 |

FOREIGN PATENT DOCUMENTS

| | | |
|---|---|---|
| WO | WO 93/09239 | 5/1993 |
| WO | WO 94/13788 | 6/1994 |
| WO | WO 9506743 A2 * | 3/1995 |
| WO | WO 98/09524 | 3/1998 |
| WO | WO 01/25465 | 4/2001 |

OTHER PUBLICATIONS

Maxwell et al. An adenovirus type 5 mutant with the preterminal protein gene deleted efficiently provides helper functions for the production of recombinant adeno-associated virus. J Virol. vol. 72, No. 10, pp. 8371-8373, Oct. 1998.*
Duan et al. (Virology. 1999; 261:8-14).*
Musatov et al. (Journal of Virology. Dec. 2002; 76(24): 12792-12802).*
Allen et al., Identification and Elimination of Replication-Competent Adeno-Associated Virus (AAV) That Can Arise by Nonhomologous Recombination during AAV Vector Production, Journal of Virology, vol. 71:6816-6822 (1997).
Lusby et al., Nucleotide Sequence of the Inverted Terminal Repetition in Adeno-Associated Virus DNA, Journal of Virology, vol. 34:402-209 (1980).
Mishra et al., Adeno-associated Virus DNA Replication is Induced by Genes That Are Essential for HSV-1 DNA Synthesis, Virology, vol. 179:632-639 (1990).
Wang et al., Rescue and Replication of Adeno-Associated Virus Type 2 as well as Vector DNA Sequences from Recombinant Plasmids Containing Deletions in the Viral Inverted Terminal Repeats: Selective Encapsidation of Viral Genomes in Progeny Virions, Journal of Virology, vol. 70:1668-1677 (1996).
Wang et al., Adeno-Associated Virus Type 2 DNA Replication in Vivo: Mutation Analyses of the D Sequence in Viral Inverted Terminal Repeats, Journal of Virology, vol. 71:3077-3082 (1997).
Samulski et al., Rescue of Adeno-Associated Virus from Recombinant Plasmids: Gene Correction within the Terminal Repeats of AAV, Cell, vol. 33:135-143 (1983).

* cited by examiner

*Primary Examiner* — Scott Long
(74) *Attorney, Agent, or Firm* — Klauber & Jackson LLC

(57) ABSTRACT

Sequences are provided that are capable of directing circular adeno-associated virus replication, useful in vectors for providing therapeutic agents to a subject in need thereof. The vectors of the invention are particularly useful in the treatment of acute medical conditions requiring rapid gene expression. Further provided are methods for producing packaged defective viral vectors.

37 Claims, 8 Drawing Sheets pTRT
```
                    trs                        Rbs
AGGAACCCTAGTGATGGAGTTGGCCACTCCCTCTCTGCGCGCTCGCTCGCTCACTGAGGCCGCCCGGGCAAAGCCCGGGCGT
        D                    A                              C'C
                     Rbs                         trs
CGGGCGACCTTTGGTCGCCCGGCCTCAGTGAGCGAGCGAGCGCGCAGAGAGGGAGTGGCCAACTCCATCACTAGGGGTTCCT
      B/B'                   A                          D
``` pBB'AD
```
                                   Rbs                         trs
GGGCGTCGGGCGACCTTTGGTCGCCCGGCCTCAGTGAGCGAGCGAGCGCGCAGAGAGGGAGTGGCCAACTCCATCACTAGGGGTTCCT
         B/B'                      A                           D
``` pBB'Atrs
```
                                   Rbs                         trs
GGGCGTCGGGCGACCTTTGGTCGCCCGGCCTCAGTGAGCGAGCGAGCGCGCAGAGAGGGAGTGGCCAACT
         B/B'                      A                           D
``` pAD
```
                              Rbs                         trs
                    GCCTCAGTGAGCGAGCGAGCGCGCAGAGAGGGAGTGGCCAACTCCATCACTAGGGGTTCCT
                                 A                           D
``` pAtrs
```
                              Rbs                         trs
                    GCCTCAGTGAGCGAGCGAGCGCGCAGAGAGGGAGTGGCCAACT
                                 A                           D
``` pDtrs
```
                                                       trs
                                                    CCAACTCCATCACTAGGGGTTCCT
                                                           D
``` pEGFP  ——————————— pAD
```
                              Rbs                         trs
                    GCCTCAGTGAGCGAGCGAGCGCGCAGAGAGGGAGTGGCCAACTCCATCACTAGGGGTTCCT
                                 A                           D
```
pAD
```
                              Rbs                         trs
                    GCCTCAGTGAGCGAGCGAGCGCGCAGAGAGGGAGTGGCCDDCTCCATCACTAGGGGTTCCT
                                 A                           D
```

Figure 1

SEQUENCE LISTING

<160> NUMBER OF SEQ ID NOS: 20

<210> SEQ ID NO 1
<211> LENGTH: 22
<212> TYPE: DNA
<213> ORGANISM: Adeno-associated virus

<400> SEQUENCE: 1
cgcccgggca agcccgggc gt                                          22

<210> SEQ ID NO 2
<211> LENGTH: 48
<212> TYPE: DNA
<213> ORGANISM: Adeno-associated virus

<400> SEQUENCE: 2
cgggcgacct ttggtcgccc ggggcgtcgg gcgacctttg gtcgcccg              48

<210> SEQ ID NO 3
<211> LENGTH: 82
<212> TYPE: DNA
<213> ORGANISM: Adeno-associated virus

<400> SEQUENCE: 3
ttggccactc cctctctgcg cgctcgctcg ctcactgagg cgcctcagtg agcgagcgag   60
cgcgcagaga gggagtggcc aa                                           82

<210> SEQ ID NO 4
<211> LENGTH: 40
<212> TYPE: DNA
<213> ORGANISM: Adeno-associated virus

<400> SEQUENCE: 4
aggaacccct agtgatggag ctccatcact aggggttcct                       40

<210> SEQ ID NO 5
<211> LENGTH: 16
<212> TYPE: DNA
<213> ORGANISM: Adeno-associated virus

<400> SEQUENCE: 5
gagcgagcga gcgcgc                                                 16

<210> SEQ ID NO 6

```
<211> LENGTH: 6
<212> TYPE: DNA
<213> ORGANISM: Adeno-associated virus

<400> SEQUENCE: 6 ccaact                                                                    6

<210> SEQ ID NO 7
<211> LENGTH: 22
<212> TYPE: DNA
<213> ORGANISM: Adeno-associated virus

<400> SEQUENCE: 7
tagtcctgtc gggtttcgcc ac                                                 22

<210> SEQ ID NO 8
<211> LENGTH: 20
<212> TYPE: DNA
<213> ORGANISM: Adeno-associated virus

<400> SEQUENCE: 8
caagtgggca gtttaccgta                                                    20

<210> SEQ ID NO 9
<211> LENGTH: 20
<212> TYPE: DNA
<213> ORGANISM: Adeno-associated virus

<400> SEQUENCE: 9
gcgcgcataa gccagtagag                                                    20

<210> SEQ ID NO 10
<211> LENGTH: 20
<212> TYPE: DNA
<213> ORGANISM: Adeno-associated virus
<220> FEATURE:
<223> OTHER INFORMATION: primer

<400> SEQUENCE: 10
ccacctctga cttgagcgtc                                                    20

<210> SEQ ID NO 11
<211> LENGTH: 20
<212> TYPE: DNA
<213> ORGANISM: Adeno-associated virus
<220> FEATURE:
<223> OTHER INFORMATION: primer

<400> SEQUENCE: 11
tggcgttact atgggaacat                                                    20

<210> SEQ ID NO 12
<211> LENGTH: 21
<212> TYPE: DNA
<213> ORGANISM: Adeno-associated virus
<220> FEATURE:
<223> OTHER INFORMATION: primer

<400> SEQUENCE: 12
acaatggcca gggccaggca g                                                  21

<210> SEQ ID NO 13
<211> LENGTH: 165
<212> TYPE: DNA
<213> ORGANISM: Adeno-associated virus
```

```
<400> SEQUENCE: 13
aggaacccct agtgatggag ttggccactc cctctctgcg cgctcgctcg ctcactgagg    60 ccgcccggc  aaagcccggg cgtcgggcga cctttggtcg cccggcctca gtgagcgagc   120
gagcgcgcag agagggagtg gccaactcca tcactagggg ttcct                   165

<210> SEQ ID NO 14
<211> LENGTH: 88
<212> TYPE: DNA
<213> ORGANISM: Adeno-associated virus

<400> SEQUENCE: 14
gggcgtcggg cgacctttgg tcgcccggcc tcagtgagcg agcgagcgcg cagagaggga    60
gtggccaact ccatcactag gggttcct                                       88

<210> SEQ ID NO 15
<211> LENGTH: 70
<212> TYPE: DNA
<213> ORGANISM: Adeno-associated virus

<400> SEQUENCE: 15
gggcgtcggg cgacctttgg tcgcccggcc tcagtgagcg agcgagcgcg cagagaggga    60
gtggccaact                                                           70

<210> SEQ ID NO 16
<211> LENGTH: 61
<212> TYPE: DNA
<213> ORGANISM: Adeno-associated virus

<400> SEQUENCE: 16
gcctcagtga gcgagcgagc gcgcagagag ggagtggcca actccatcac taggggttcc    60
t                                                                    61

<210> SEQ ID NO 17
<211> LENGTH: 43
<212> TYPE: DNA
<213> ORGANISM: Adeno-associated virus

<400> SEQUENCE: 17
gcctcagtga gcgagcgagc gcgcagagag ggagtggcca act                      43

<210> SEQ ID NO 18
<211> LENGTH: 24
<212> TYPE: DNA
<213> ORGANISM: Adeno-associated virus

<400> SEQUENCE: 18
ccaactccat cactagggt tcct                                            24

<210> SEQ ID NO 19
<211> LENGTH: 61
<212> TYPE: DNA
<213> ORGANISM: Adeno-associated virus

<400> SEQUENCE: 19
gcctcagtga gcgagcgagc gcgcagagag ggagtggccd dctccatcac tagggggttcc   60 t                                                                    61

<210> SEQ ID NO 20
<211> LENGTH: 86
<212> TYPE: DNA
```

<213> ORGANISM: Adeno-associated virus

<400> SEQUENCE: 20

```
catgtggtca cgctgggtat ttaagcccga gtgagcacgc agggtctcca ttttgaagcg      60
ggaggtttga acgcgcagcc gccatg                                           86
```

METHOD FOR GENERATING REPLICATION DEFECTIVE VIRAL VECTORS THAT ARE HELPER FREE

RELATIONSHIP TO OTHER PATENT APPLICATIONS

This application claims priority to U.S. provisional applications 60/294,797 filed May 31, 2001, and No. 60/313,007 filed Aug. 17, 2001, both of which applications are herein specifically incorporated by reference in their entirety.

FIELD OF THE INVENTION

The present invention provides a method of producing defective viral vectors for gene therapy that are completely free of helper viral vectors and helper viruses. The invention further provides new circular AAV vectors which are particularly useful for use in gene therapy and production stocks of packaged defective viral vectors.

BACKGROUND

Gene therapy is likely to become the most significant development in medicine of our time. However, before gene therapy becomes a standard medical procedure, certain technical problems common to all methods of gene delivery must be overcome. One key obstacle is the current inability to produce large quantities of pure replication defective viral vectors.

Indeed, most gene therapy protocols use replication defective viral vectors as gene therapy vehicles. This is due to the ability of viruses to efficiently transfect their own DNA into a host cell. By replacing viral genes that are needed for the replication (the non-essential genes) with heterologous genes of interest, replication defective viral vectors can transduce the host cell and thereby provide the desired genetic material to the host cell. The non-essential genes can be provided in trans in order to produce the replication defective viral vectors. Thus the non-essential genes are placed into the genome of the packaging cell line, on a plasmid, or a helper virus. A number of replication defective viral vectors have been constructed, though most of the work has centered on three particular DNA viruses; the adenovirus, the adeno-associated virus and the herpes simplex virus type 1.

Adeno-associated virus type 2 (AAV) is a human non-pathogenic parvovirus with a genome of approximately 4.7 kb. The AAV genome consists of two ORFs that encode regulatory (Rep) and structural capsid (Cap) proteins flanked by 145-bp inverted terminal repeats (ITR). These ITRs are the only cis-acting elements necessary for virus replication and encapsidation. Recombinant AAVs (rAAV) which do not contain any endogenous coding regions efficiently propagate when Rep and Cap are provided in trans. In nature, a secondary infection with helper virus, e.g. adenovirus, is necessary to trigger a productive infection. AAV genomes then undergo replication followed by assembly of infectious virions containing ssDNA of either (+) or (−) polarity. Adenovirus genes implicated in AAV replication have been identified and include E1A, E1B, E4orf6, E2A, and VA RNA.

Similar to provirus in latently infected cells, AAV genomes can be efficiently rescued from a recombinant cis-plasmid following transient transfection into human cells. The necessary helper functions can be delivered either by adenovirus infection or by transfecting a plasmid encoding a minimal set of adenovirus helper genes (Collaco et al. (1999) Gene 238: 397-405).

Events of AAV lytic infection are described by a commonly accepted self-priming strand-displacement model. The first 125 nucleotides of AAV termini include elements capable of forming a T-shaped duplex structure (A'-B'-B-C'-C-A) and are followed by a unique 20 bp D-sequence (Wang et al. (1995) J. Mol. Biol. 250:573-580). The Rep gene encodes four proteins that are synthesized from the same ORF via the use of alternate promoters and splicing. Two of these proteins (Rep78 and Rep68) possess site-specific and strand-specific endonuclease activity. They bind to the Rep-binding site (Rbs) mapped to the tetrameric GAGC repeat of the A-stem of the ITR and cleave it at the terminal resolution site (trs), positioned between the A- and D-elements. A tip of the BB' palindrome contains RBE', a cis-acting element essential for optimal Rep-specific activity. During replication, the terminus folds on itself and serves as a primer to initiate a leading-strand synthesis. At the elongation step, the complementary strand is displaced and may serve as an independent second replication template. The result of this first round of DNA synthesis is a linear duplex replication form monomer (Rfm) with a covalently closed hairpin on one end. Rep-mediated nicking of the original strand then creates a 3'-OH primer and the hairpin is extended. If nicking and subsequent ITR repair do not occur before the second round of replication is initiated on an opposite newly formed 3' end, then continued DNA synthesis leads to formation of a replication form dimer (Rfd), which can be organized head-to-head (H-H) or tail-to-tail (T-T), but never head-to-tail. The model also predicts that linear duplex structures are intermediates of packaging. Using these as a template, the other two Rep proteins (Rep52 and Rep40) generate single-stranded progeny genomes which are then encapsidated into preformed capsids.

One of the great challenges in effectively applying gene therapy to human disease is the development of simple systems for rapidly generating high volumes of high titer viruses completely uncontaminated by potentially toxic helper viruses. One approach has been the development of techniques for producing "defective" viral vectors devoid of helper viruses. The most popular vectors include adeno-associated virus (AAV) and "gutless" adenovirus vectors which contain only the ITRs and a packaging sequence round the transgene. These harbor no viral genes, are incapable of replication, and helper viruses can be completely eliminated. Current strategies for producing such vectors, however, rely on techniques which either limit viral titers or which are so labor and resource intensive that they severely limit the clinical and commercial viability of these promising systems.

In an attempt to overcome this critical problem, new approaches have been attempted, though heretofore with limited success. In one such approach, a herpes amplicon system was created in which essential AAV genes (Rep and Cap) were inserted into the amplicon, and a second "helper" herpes simplex virus (HSV) was used to package the amplicon. The mix was then used to package AAV vector. This helper HSV virion was a mutant HSV that contained a mutation in a gene that is necessary for HSV infection, i.e., the glycoprotein H (gH) (Zhang et al., 1999, Hum. Gen. Ther. 10(15):2527-2537).

U.S. Pat. No. 5,139,941 (Muzyczka et al.) describes a AAV vector having the first and last 145 bp containing the ITRs, and capable of tranducing foreign DNA into a mammalian cell. U.S. Pat. No. 5,478,745 (Samulski et al.) describes a 165 bp fragment containing an AAV 145 bp ITR sequence with the 20 bp D sequence found to provide sufficient information in cis for replication and encapsidation of recombinant DNA fragments into mature AAV virions. U.S. Pat. No. 5,436,146 (Shenk et al.) describe helper free stocks of recombinant AAV vectors. Collaco et al. (1999) Gene 238:397-405 describe a helper virus-free packaging system for recombinant AAV vectors.

SUMMARY OF THE INVENTION

The present invention provides helper free, fully defective viral vectors produced with high titers. The novel vectors of the invention are based, in part, on the initial discovery of a minimal 61 bp AD sequence required for circular AAV replication. This 61 bp sequence (SEQ ID NO: 16) acts as both an origin of circular AAV (cAAV) replication and a packaging signal.

Further studies of cAAV replication revealed that the sequence required for replication is a sequence comprising TGGCCAA ("the loop sequence") flanked on each side by complementary sequences, such that a hairpin structure is formed by the complementary sequences hybridizing to each other. The flanking complementary sequences may be any complementary sequences of any length. In one embodiment, the flanking complementary sequences may be 5-10 bp in length. In a preferred embodiment, the flanking sequences are 7 bp in length. Further experiments have shown that a one base mismatch in the complementary flanking sequences provides improved replication. Accordingly, in a specific embodiment, the complementary flanking sequences comprise a one base mismatch. In a more specific embodiment, base 5 of a 7 base complementary flanking sequence contains a mismatched base.

According, in a first aspect, the invention features a nucleotide sequence capable of directing circular adeno-associated virus replication, comprising a loop sequence TGGCCAA flanked on the 5' and 3' sides by complementary sequences, wherein a hairpin structure is formed between the complementary sequences. In one embodiment, the complementary flanking sequences are between 5-10 base pairs in length. In a more specific embodiment, the complementary sequences are 7 base pairs in length. In one embodiment, the complementary flanking sequences comprise a one base mismatch, resulting in improved cAAV replication. In a more specific embodiment, the complementary sequences are 7 base pairs in length, and the mismatch is at base 5. In one embodiment, the nucleotide sequence capable of directing circular adeno-associated virus replication is about 61 bp in total length. In a more specific embodiment, the nucleotide sequence is SEQ ID NO: 16.

In a second related aspect, the invention features a helper-free fully defective cAAV vector comprising the (i) at least one of the nucleotide sequence of SEQ ID NO: 16, and (ii) a heterologous nucleic acid sequence encoding a protein of interest. In more specific embodiment, the vector of the invention comprises two of the nucleotide sequence having the sequence of SEQ ID NO: 16.

The cAAV vector of the invention possesses several important features not found in prior art vectors. For example, in one embodiment, the cAAV vector of the invention preferably retains one 61 bp AAV sequence, providing increased capacity for insertion of foreign DNA by eliminating an additional 230 bp of viral sequences relative to prior art vectors. In another embodiment, the cAAV vector retains two 61 bp AAV sequences. Further, as shown in the Examples below, this vector is capable of being packaged such that it is suitable for use in gene therapy applications. Still further, the cAAV vector of the invention provides improved short term expression of a gene of interest and thus provides an important advantage for use in treatment of acute conditions requiring rapid expression of a therapeutic gene of interest.

In more specific embodiments, the defective cAAV vector of the invention comprises a nucleic acid sequence encoding a protein of interest operably linked to a promoter sequence. In more specific embodiments, the promoter is an inducible promoter. In even more specific embodiments, the inducible promoter is selected from the group consisting of a metallothionein promoter, a tetracycline promoter, or a heat shock protein promoter.

In another embodiment, the cAAV vector of the invention comprises a nucleic acid sequence encoding a therapeutic protein of interest. In more specific embodiments, the therapeutic protein of interest is selected from the group consisting of a a hormone, e.g., insulin; an enzyme, such as tyrosine hydroxylase, adenosine deaminase, phenylalanine hydroxylase; or a growth factor, e.g., glial-derived neurotrophic factor (GDNF), nerve growth factor (NGF).

In a third aspect, the invention features a method of treating an acute medical condition in a subject in need thereof, comprising administering a circular adeno-associated virus (cAAV)-derived vector comprising at least one 61 bp element comprising the sequence of SEQ ID NO: 16, and a nucleic acid sequence encoding a therapeutic protein of interest operably linked to a promoter sequence, wherein the therapeutic protein is expressed within 1 day after administration of the cAAV-derived vector.

In other embodiments, expression is achieved within 8-24 hours after administration; preferably within 8-12 hours. In a further embodiment, expression is achieved within 24 hours and expression is increased 10 fold within 48 hours.

In a fourth aspect, the present invention provides methods for preparing helper free, fully defective cAAV and traditional AAV vectors that can be produced with high titers. In one embodiment of this method, a replication-defective helper viral vector is employed that comprises (i) at least one heterologous nucleic acid which is necessary but not sufficient for the replication and packaging of a defective viral vector, and (ii) requires the expression and/or transcription of at least one exogenous nucleic acid to replicate (and/or to be packaged). The replication-defective helper viral vector and the defective viral vector are placed into a permissive cell that contains the exogenous nucleic acid(s) required to replicate and preferably package the replication defective helper viral vector and any remaining genes required to replicate and preferably package the defective viral vector. Thus, in the permissive cell, the replication-defective helper viral vector is replicated and preferably packaged and the defective viral vector is replicated and packaged. The resulting mixture of replication-defective helper viral vector and defective viral vector is termed the production stock.

In a fifth aspect, the present invention provides for a method of propagating cAAV-derived vectors and growing to high titer. In one embodiment of this method, the initial cAAV-derived stock is used to co-infect fresh cells with a helper adenovirus. The resulting mixed stock is then used to re-infect fresh cells, and this is then repeatedly re-used as necessary. The cAAV-derived vectors are then purified and separated from the adenovirus by column purification. In another embodiment of this method, the helper adenovirus is replaced by helper herpes simplex virus. In a preferred embodiment, the initial cAAV-derived stock is used to infect cells expressing the adenovirus E1a, E2a, E4, VA RNA gene products and the AAV rep and cap gene products ("necessary adenovirus and AAV gene products"). The resulting stock can be used to re-infect fresh cells expressing these gene products, and this is then repeatedly re-used as necessary. No helper virus is produced by this method, so the cAAV-derived vectors generated by this method are simply purified from cellular debris. In another embodiment of this method, the cells used are 293 cells, which endogenously express the adenovirus E1a gene product. In another embodiment of this method, the necessary adenovirus and AAV gene products are provided by a plasmid which is transfected into cells prior to infection with the cAAV-derived stock. In another embodiment of this method, a cell-line is used which endogenously expresses the adenovirus and AAV gene products necessary for cAAV-derived vector propagation.

The production stock of replication-defective helper viral vector (packaged or not) and packaged defective viral vector can be amplified by co-infecting another permissive cell. This amplification can be repeated until a desired titer is obtained. When a desired titer is achieved, the production stock of replication-defective helper viral vector and packaged defective viral vector is placed into a non-permissive cell which comprises the heterologous nucleic acid(s) required to replicate and package the defective viral vector in conjunction with the heterologous nucleic acid of the defective helper viral vector, but is missing the exogenous nucleic acid(s) required to replicate the replication defective helper viral vector.

In a sixth aspect, the invention features a defective helper vector for use in the production of a packaged defective viral vector. A defective helper vector of the present invention requires the expression and/or transcription of one or more exogenous nucleic acid(s) to replicate and/or be packaged and preferably comprises one or more heterologous nucleic acid(s) that aids in the replication and/or packaging of a defective viral vector.

In one embodiment, the defective helper vector is a modified virus. In more specific embodiments, the modified virus is a cytomegalovirus (CMV), an adenovirus (Ad), a simian vacuolating virus 40 (SV40), a human papillomavirus (HPV), a Hepatitis B virus, a JC papovaviridae virus, an Esptein Bar Virus (EBV), or a herpes simplex virus (HSV). In a more specific embodiment, the defective helper vector is a modified HSV that lacks both copies of its ICP4 gene, and comprises the adenoviral genes E1A, E2a, E4orf6, and VAI RNA. In another specific embodiment, the defective helper vector comprises E1A, E2a, E4orf6, and VAII RNA in place of VAI RNA. In another specific embodiment, the defective helper vector comprises E1A, E2a, E4orf6, and both VAI RNA and VAII RNA. Preferably the defective helper vector further comprises the adenoviral gene E1B.

In a seventh aspect, the present invention features a composition comprising a defective helper vector of the present invention combined with a defective viral vector. In one embodiment, this composition is a production stock of defective helper vector and packaged defective viral vector. In another embodiment the composition is a production stock of packaged defective helper vector and packaged defective viral vector. In a more specific embodiment, the defective viral vector is the circular adeno-associated virus (cAAV)-derived vector described above and in the following Examples.

In an eighth aspect, the invention provides mammalian cells that comprise a plasmid encoding the AAV genes Rep and Cap. Preferably the plasmid has an Epstein-Barr Viral origin of replication. In an alternative embodiment, the mammalian cell further encodes the HSV gene ICP4. In a specific embodiment, the mammalian cell encodes Cap, E4orf6 and E2a under the control of inducible promoters that are inducible by a first inducer and Rep under the control of an inducible promoter inducible by a second inducer, wherein the mammalian cell also expresses both VAI RNA and E1A. In one embodiment, the mammalian cell further expresses E1B.

In another embodiment, the inducible promoters that are inducible by a first inducer are tet-responsive promoters. In yet another embodiment, the inducible promoter inducible by a second inducer is a metallothionein promoter.

In a ninth aspect, the invention provides methods for generating a production stock of packaged defective viral vectors and defective helper vectors. Preferably the production stock comprises of packaged defective viral vectors and packaged defective helper vectors. One such method comprises placing a defective helper vector and a defective viral vector into a permissive cell and thereby allowing the defective viral vector and the defective helper vector to be replicated and at least the defective viral vector be packaged. Preferably the dhlpv comprises (i) one or more helper heterologous nucleic acid(s), the expression and/or transcription of which are necessary but not sufficient for the replication or packaging of the defective viral vector in the permissive cell, but (ii) further requires the expression and/or transcription of one or more exogenous nucleic acid(s) to replicate and be packaged. The permissive cell preferably comprises (i) the exogenous nucleic acid(s) required to replicate and package the dhlpv, and (ii) further comprises one or more ancillary heterologous nucleic acids, the expression and/or transcription of which in conjunction with the expression and/or transcription of the helper heterologous nucleic acid(s) enables the replication and/or packaging of the defective viral vector in the permissive cell thereby allowing a production stock of packaged dhlpv and dvv to be generated.

In a particular embodiment of this type, the dvv further comprises a heterologous nucleic acid of interest. In a preferred embodiment of this type, the dvv is a defective AAV vector. In another embodiment the dvv is a gutless adenoviral vector. A production stock generated by a method of the present invention is also part of the present invention.

A production stock of the present invention obtained by any of the methods of the present invention can be further amplified by placing (e.g., co-infecting) the defective helper vector and the packaged defective viral vector of the production stock into a fresh permissive cell. This process can may be repeated as desired to further increase/optimize the titer.

In a tenth aspect, the invention provides kits for preparing a production stock of packaged defective viral vectors (dvv) and defective helper vectors (dhlpv). In one embodiment, the kit comprises a defective helper vector of the present invention and a packaged defective viral vector. A preferred embodiment includes a permissive cell that comprises: (i) one or more exogenous nucleic acid(s) required to replicate (and preferably) package the dhlpv, and (ii) one or more ancillary heterologous nucleic acids, the expression and/or transcription of which in conjunction with the expression and/or transcription of the helper heterologous nucleic acid(s) enables the replication and packaging of the defective viral vector in the permissive cell. In a more specific embodiment, the kit further comprises a non-permissive cell that (i) does not comprise one or more exogenous nucleic acid(s) required to replicate the dhlpv, but does comprise (ii) one or more ancillary heterologous nucleic acids, the expression and/or transcription of which in conjunction with the expression and/or transcription of the helper heterologous nucleic acid(s) enables the replication and packaging of the defective viral vector in the non-permissive cell. Preferably a kit of the present invention further comprises a protocol for producing the helper free defective viral vectors.

In an eleventh aspect, the invention features a packaging system for generating a helper-free defective viral vector. One such method comprises placing (e.g., co-infecting) a production stock of defective helper vector and packaged defective viral vector into a non-permissive cell that comprises one or more ancillary heterologous nucleic acids, the expression and/or transcription of which in conjunction with the expression and/or transcription of the helper heterologous nucleic acid(s) enables the replication and/or packaging of the defective viral vector in the non-permissive cell. However, the replication and/or packaging of the dhlpv is prevented because the non-permissive cell does not comprise the exogenous nucleic acid(s) required. Thus, a helper-free defective viral vector is obtained.

In a twelfth aspect, the invention further provides methods of delivering a gene of interest to a target tissue of an animal subject using a helper-free defective viral vector of the present invention. One such method comprises administering the vector directly to the tissue of the animal subject. In addition, the present invention provides a non-human mammalian host transformed with a helper-free defective viral vector of the present invention. Such non-human mammalian hosts can be used as animal model for treatment and/or curing of a condition or disease.

Useful in the method of the invention are the use of recombination sequences recognized by a recombinase enzyme. Such methods are described in, for example, U.S. Pat. No. 6,350,575 (Lusky et al.), which publication is herein specifically incorporated by reference in its entirety.

Other objects and advantages will become apparent from a review of the ensuing detailed description taken in conjunction with the following illustrative drawings.

BRIEF DESCRIPTION OF THE DRAWINGS

FIG. 1 shows the sequences for pTRT (SEQ ID NO: 13), pBB'AD (SEQ ID NO: 14), pBB'Atrs (SEQ ID NO:15), pAD (SEQ ID NO: 16), pAtrs (SEQ ID NO:17), pDtrs (SEQ ID NO: 18), and a pAD mutant (SEQ ID NO: 19).

FIG. 2: Restriction maps of predicted replicative intermediates: a linear monomer (Rfm), circular monomer (cAAV), head-to-head dimer (Rfd, H-H), and tail-to-tail dimer (Rfd, T-T). ITRs are represented by arrows, while the TRT domain is shown as a black box. Vertical lines indicate positions of XbaI sites. The sizes of the fragments liberated following XbaI cleavage and recognized by the CMV promoter-specific probe (dotted line) are shown next to corresponding structures. The position of a 1.2-kb fragment released by DpnI from input plasmids is also indicated. FIG. 3: Replication of constructs shown in FIG. 1 following co-transfection with pAd.Help.Rep.Cap.zeo into 293 cells. Hirt DNA was extracted 72-h post-transfection and 5% of the total yield from a 35-mm culture well was digested with DpnI alone or DpnI and XbaI. Samples were resolved on a 0.9% agarose gel and the blots were hybridized with a $^{32}$P-labeled CMV promoter probe. The relative migration of 1-kb size markers is shown to the left of the blot. The AAV replicative intermediates as well as the input plasmid are indicated along the right side of the blot. FIG. 4: replication of the same cAAV constructs after co-trasfection with pRep.Cap into adenovirus-infected 293 cells. Cells were harvested 48-h post-transfection and samples were analyzed as described for blot (FIG. 3).

FIG. 5: Schematic representation of pCis and pAD. Positions of XbaI sites are indicated. ITRs of pCis are drawn as arrows and the AD domain of pAD is denoted as a box. XbaI cleavage of DpnI-resistant circular species followed by hybridization with a CMV promoter-specific probe (dotted line) is expected to produce 2.5-kb and 3.2-kb bands for pCis and pAD, respectively. cAAVs assembled during pCis replication are similar in size and structure to pAD except that they contain the TRT domain. Since pCis would generate the TRT domain that is slightly larger than the AD domain, cAAVs derived from pCis would produce a band of 3.5 kb instead of 3.2 kb. FIG. 6: pCis and pAD were assayed for replication as described in the legend of FIG. 3. Note that linear forms are present in pCis replication, but they are absent in pAD replication. The relative migration of 1-kb size markers is shown to the left of the blot. Replicative intermediates are the same shown in FIG. 1 and are labeled along the right side of the blot.

DETAILED DESCRIPTION

Figure 2:
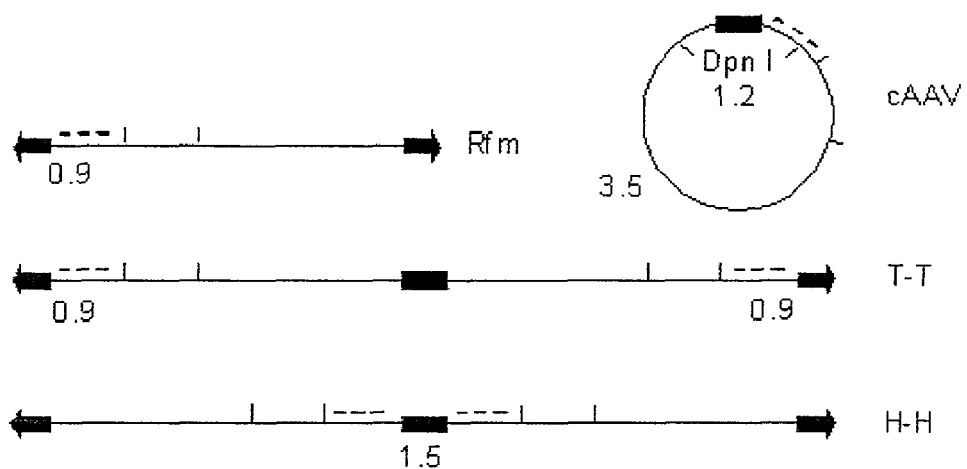
FIGS. 2-4. Southern blot analysis of replication of cAAV genomes containing deletions in ITRs.

Before the present methods and treatment methodology are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

Definitions

The term "gene" refers to an assembly of nucleotides that encodes a polypeptide. A gene, as used in the present invention, includes both cDNA and genomic DNA nucleic acids and therefore, does not necessarily correspond to the naturally occurring gene which contains all of the introns and regulatory sequences, present in the natural genomic DNA; a gene can merely contain a coding sequence for a particular protein.

A "vector" as used herein is a genetic construct that facilitates the efficient transfer of a nucleic acid (e.g., a gene) to a cell. The use of a vector can also facilitate the transcription and/or expression of that nucleic acid in that cell. Examples of vectors include plasmids, phages, amplicons, viruses and cosmids, to which another DNA segment may be attached so as to bring about the replication of the attached segment.

A "viral particle" is a vector that has been packaged in viral proteins, i.e., a viral coat.

A vector is "packaged" when it is placed into a viral coat as part of a virus or viral particle.

As used herein, a "heterologous nucleic acid" is a nucleic acid that has been placed into a vector or cell that does not naturally comprise that nucleic acid. In one embodiment, a heterologous nucleic acid encodes a protein, i.e., a "heterologous gene" and but can also comprise a regulatory sequence without a coding sequence (e.g., a specific promoter), an antisense nucleic acid, a ribozyme, a tRNA or other nucleic acid.

As used herein a "helper heterologous nucleic acid" is a heterologous nucleic acid comprised by a helper vector. An "ancillary heterologous nucleic acid" is a heterologous nucleic acid that is not comprised by the helper vector. This denotation is made solely to distinguish the location of a particular heterologous nucleic acid.

As "heterologous or foreign nucleic acid of interest" is a heterologous nucleic acid that has been placed into a defective viral vector for reasons other than to promote viral replication and/or viral packaging. In one embodiment, the heterologous nucleic acid has been placed into a defective viral vector for an ultimate therapeutic use in a gene therapy protocol, and/or as a marker. In a particular embodiment, the heterologous nucleic acid of interest encodes a protein.

A nucleic acid is "exogenous" to a vector when the nucleic acid is not comprised by the vector. The gene product of the vector can then be supplied by either a second vector and/or a permissive host cell which contains the exogenous nucleic acid. As exemplified below, an exogenous nucleic acid is contained by the permissive cell and is required for the replication and/or packaging of the defective helper viral vector.

A "defective viral vector", abbreviated "dvv" is a viral vector that requires the expression and/or transcription of at least one nucleic acid that it lacks in order to be replicated and/or packaged. In one embodiment, the dvv is a replication defective viral vector. In a more specific embodiment, a defective viral vector also comprises a heterologous nucleic acid of interest. More specifically, a defective viral vector comprises a minimum number of viral genes, and more preferably does not encode a viral protein.

The term "defective helper vector", abbreviated as "dhlpv" is used interchangeably with the term "replication defective helper vector" and is a vector that requires the expression and/or transcription of at least one nucleic acid that it lacks in order to be replicated. A dhlpv also encodes at least one nucleic acid that when expressed and/or transcribed in a cell can aid in the replication or packaging of a defective viral vector. In the examples below, the dhlpv comprises heterologous nucleic acids that aid in the replication or packaging of a defective viral vector.

As used herein, a "permissive cell line" is a cell line (or cell) in which a replication defective helper vector can replicate, and a defective viral vector can be replicated and packaged. A "non-permissive cell line" is a cell line (or cell) in which the replication defective helper vector contained in a mixture of a defective helper vector and a defective viral vector cannot replicate but the defective viral vector can be replicated and packaged. Therefore, whereas a defective viral vector can be replicated and packaged in its corresponding non-permissive cell line, the non-permissive cell line does not support the replication of the corresponding defective helper vector, as exemplified below.

"Production stock" is a composition comprising a defective helper vector (preferably packaged) and a packaged defective viral vector. A production stock can be used to generate additional packaged defective viral vector and defective helper virus when placed into a permissive cell. In can also be used to generate helper free packaged defective viral vector when placed into a non-permissive cell. In a particular embodiment, the production stock is comprised of a packaged defective helper virus and a packaged defective viral vector.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "operatively under the control" of transcriptional and translational control sequences in a cell when RNA polymerase transcribes the coding sequence into a precursor RNA, which is then trans-RNA spliced to yield mRNA and translated into the protein encoded by the coding sequence.

A nucleotide sequence is "operatively under the control" of a genetic regulatory sequence when the genetic regulatory sequence controls and/or regulates the transcription of that nucleotide sequence. That genetic regulatory sequence can also be referred to as being "operatively linked" to that nucleotide sequence.

A "genetic regulatory sequence" is a nucleic acid that: (a) acts in cis to control and/or regulate the transcription of a nucleotide sequence, and (b) can be acted upon in trans by a regulatory stimulus to promote and/or inhibit the expression of the nucleotide sequence. Therefore, an inducible promoter is a genetic regulatory sequence. In addition, a portion of a promoter (e.g., fragment/element) that retains and/or possesses the ability to control and/or regulate the expression of a nucleotide sequence either alone or in conjunction with an alternative promoter or fragment thereof (e.g., a chimeric promoter) is also a genetic regulatory sequence. Such fragments include, response elements (genetic response elements) and promoter elements.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a nucleic acid that one desires to insert into a recombinant DNA molecule does not contain an appropriate start signal, such a start signal can be inserted in front of the gene.

"Treatment" refers to the administration of medicine or the performance of medical procedures with respect to a patient, for either prophylaxis (prevention) or to cure the infirmity or malady in the instance where the patient is afflicted.

General Description

The present invention provides a facile method for producing high titer, helper free, fully defective viral vectors. This method can be fully automated using a "mixed virus" system and multiple cell lines which permits ready amplification and renewal of the vector stock, while also permitting production of large volumes of pure, high titer vectors. The invention also provides methods of using the high titer, helper free, fully defective viral vectors suitable for use as a method of treatment in a gene therapy protocol.

The studies below demonstrate that a 61 bp AD sequence (SEQ ID NO:16) functions as both an original of circular AAV replication and a packaging signal. The identified cis-acting replication element encompasses the A-stem and the D-sequence with an intact trs and apparently does not require any other ITR domains. A vector comprising the 61 bp AD sequence is particularly useful for treatment of acute medical conditions where rapid expression of a therapeutic gene, e.g,. within 8-12 hours or 1-2 days, is required to achieve improvement or to prevent damage to a subject suffering the acute medical condition. Acute medical conditions that would benefit from early expression of a therapeutic agent include neurodegenerative diseases (such as Parkinson's disease), strokes, cardiovascular episodes, and some types of tumors. The vector of the invention comprising the 61 bp AD sequence is also useful in gene therapy requiring long term expression.

The present invention employs a defective helper vector that is constructed to be capable of replication only in a permissive cell line. The defective helper vector is preferably constructed so as to comprise heterologous nucleic acids from at least one other virus. This ensures that the defective helper vector cannot undergo homologous recombination and revert to a harmful wild type form. It also more readily permits the removal of the defective helper vector when the defective helper vector has a viral coat that differs from that of the defective viral vectors. In any case, the heterologous nucleic acids of the defective helper vector supply at least some helper functions for at least one other viral system. Preferably the defective helper vector is constructed to supply some but not necessarily all helper functions for at least one other viral system.

In one embodiment, the permissive cell line further contains the remaining helper functions which, in conjunction with the helper heterologous nucleic acids, permit the packaging of a replication defective viral vector. The resulting packaged replication defective viral vector can be used as a gene transfer vehicle in gene therapy, to help generate transgenic non-human animals, and can be used to transform mammalian cells in culture.

In a particular aspect of the present invention, a replication defective viral vector comprising a nucleic acid of interest requires both a replication defective helper vector and the remaining helper functions supplied by the permissive cell (or an amplicon or plasmid contained by the cell) to be successfully packaged. Similarly, to replicate, the defective helper vector requires the expression of one or more heterologous genes contained by the permissive cell. Therefore, when the replication defective viral vector and the replication defective helper vector are placed into the permissive cell, they are both replicated and at least the replication defective viral vector is packaged. The replication defective helper vector and packaged replication defective viral vector together form a "production stock" that can be re-infected into fresh permissive cells to continuously produce additional replication defective helper vector and packaged replication defective viral vector.

In one embodiment, the replication defective viral vector can be purified away from the defective helper vector by placing the "production stock" in a non-permissive cell line that can provide the requisite helper functions in conjunction with the replication defective helper vector to replicate and package the replication defective viral vector, but does not support the replication of the replication defective helper vector. In the non-permissive cell the replication defective helper vector can still aid in the production of the packaged defective viral vector, but no new replication defective helper vector can be produced. The resulting stock, called the "vector stock", is pure replication defective viral vector completely free of helper viruses. The genes required to package the replication defective viral vector contained by the replication defective helper vector is preferably in a packaged virus particle. Alternatively, however, it can also be inserted in a vector plasmid and/or helper virus mix and this plasmid and/or mix may be used in lieu of and/or in conjunction with a replication defective helper virus.

Two examples described below demonstrate the ability of the present invention to produce high titers of defective viral vectors free of helper virus. The defective helper vector can be derived from HSV, cytomegalovirus, adenovirus, SV40, human papillomavirus, Hepatitis B virus, JC virus, or EBV. The defective helper vectors contain one or more deletions in an essential gene which prevents its reproduction. The defective helper vector can also contain one or more helper sequences from the wild-type virus from which the defective viral vector is derived and/or from a third virus that encodes suitable helper genes. Preferably, the replication defective helper vector is a viral particle. Additional helper sequences also may be inserted into a defective amplicon or plasmid derived from the helper virus which can be packaged along with a replication defective helper viral particle to serve as a mixed helper stock. Additional necessary helper functions may be inserted into a cell line for vector production, although this is not essential.

Vector stocks of the present invention can be produced in large scale quantities. Any defective DNA viral vector can be amplified by first being introduced into a production (i.e., permissive) cell line that expresses the key missing gene(s) necessary for reproduction of the defective helper vector and in conjunction with the defective helper vector expresses the key gene(s) necessary for reproduction and/or packaging of the defective viral vector. This results in a mix of packaged defective viral vector and defective helper vector. This production stock can then be used to re-infect larger amounts of fresh production cells, resulting in increasing amounts of packaged defective viral vector and defective helper vector.

Defective viral vector can then be purified by infecting the mix into non-permissive cells which do not contain the essential gene(s) required for the defective helper vector to replicate. This prevents reproduction of the defective viral vector, but still supports reproduction of the defective viral vector, resulting in a pure stock of defective viral vectors. Preferably the defective viral vector contains only recognition signals for replication and packaging but no viral genes.

The methodology disclosed herein therefore permits rapid packaging of any vector plasmid without the need to create new cell lines. The resulting replication defective viral vector is free of contaminating helper viruses, including "non-functional" viral particles. Furthermore, the production stock can be easily grown and amplified through repeated rounds of re-infection in permissive cells without the need to transfect new cells or add any new helper vectors/viruses. Since this is essentially a single-step process, it can be applied to automated, bioreactor settings to permit commercial-scale large volumes of "production stock". Furthermore, pure defective viral vectors can be obtained at any time by simply infecting the corresponding non-permissive cell line with the production stock.

In addition to ease of use and efficient, high volume, high titer production, the methodology provided by the present invention has the advantage of permitting the storage of high volumes of a single lot of production stock which can be readily converted to a gene therapy vehicle by the "purification" infection of the non-permissive cell line. Therefore, the present invention creates an unprecedented opportunity for quality control and lot analysis, which is essential for reliable clinical and commercial applications.

Production of Helper-Free Defective Viral Vectors

An antibiotic-sensitive cell line (such as hygromycin as exemplified below, neomycin, ampicillin, penicillin, tetracycline and the like) can be obtained and/or constructed to express a nucleic acid to produce a gene product that is required for the replication and/or packaging of a given replication-defective helper vector. This nucleic acid is referred to as an exogenous nucleic acid. The ICP4 gene of HSV is the exogenous nucleic acid described in the Examples below, and is employed along with a replication defective HSV helper vector that lacks the ICP4 gene, because the ICP4 gene product is essential for late HSV gene expression and for HSV replication.

Cells that can be used to generate permissive and non-permissive cell lines include A549, WEHI, 3T3,10T1/2, BHK, MDCK, COS 1, COS 7, BSC 1, BSC 40, BMT 10, VERO, W138, HeLa, 293, Saos, C2C12, L Cells, HT1080, HepG2, and primary fibroblasts, hepatocytes, or myoblasts. Cell lines that express Rep and Cap also have been described previously (see U.S. Pat. No. 5,658,785).

A corresponding antibiotic resistant plasmid can be constructed so as to contain one or more heterologous nucleic acids that are required for the replication and/or packaging of the replication-defective viral vector. When the heterologous nucleic acid(s) are used in conjunction with one or more heterologous nucleic acid contained by a defective helper vector, the heterologous nucleic acid(s) of the plasmid are referred herein to as ancillary heterologous nucleic acids, and the heterologous nucleic acid(s) contained by the defective helper vector can be referred to as helper heterologous nucleic acid(s).

In Example 1 below, the defective viral vector is derived from an AAV virus so two essential AAV genes, Rep and Cap were inserted into the plasmid and are the ancillary heterologous nucleic acids. In Example 2 below, the defective viral vector is a "gutless" adenoviral vector so the ancillary heterologous nucleic acids of the plasmid were a subset of the adenovirus genome containing the adenovirus genome including the essential adenoviral fiber protein, but the E1A, E1B, E2a, E4orf6, and VAI RNA sequences were deleted. When the defective helper vector and the permissive cell have heterologous nucleic acids from the same viral genome, it is preferred that no sequence overlap is maintained between the heterologous nucleic acids included in the plasmid and those included in the defective helper vector to prevent any chance of homologous recombination between the two.

In a more specific embodiment, the plasmid also contains the Epstein-Barr Virus (EBV) origin of replication and the EBNA gene. When this plasmid is introduced into this cell line, the Epstein-Barr Virus (EBV) origin of replication and the EBNA gene product permit continuous maintenance of the plasmid in an episomal state. Alternatively, the plasmid may be generated to have a particular drug resistance and then can be inserted into the cell and maintained using standard drug selection methodology (e.g., the plasmid bestows the particular drug resistance to the cell and the cells are grown in the presence of the drug).

Selection based upon antibiotic resistance allows a cell line containing the plasmid which expresses the ancillary heterologous nucleic acid(s) of the plasmid and the exogenous nucleic acid(s) of the cell. This cell line is referred to herein as the permissive cell since both the defective viral vector and the defective helper vector can be replicated and at least the defective viral vector can be packaged in the permissive cell line. A non-permissive cell line is also prepared that is analogous to the permissive cell line except the non-permissive cell line does not express the exogenous nucleic acid(s) required for the replication of the defective helper vector. As is apparent, the antibiotic resistance is only employed to allow the selection of the cells that contain the plasmid. Alternative methods of identification and isolation of cells containing the plasmid can be performed. One such method uses a plasmid encoding a marker protein (such as green fluorescent protein). Another uses an antigen marker expressed by the plasmid, along with an fluorescent antibody. In either case, the desired cells can be isolated by fluorescent cell sorting, for example.

In the Examples below, the ancillary heterologous nucleic acids (Rep/Cap) are expressed at low levels in the absence of defective helper vector, so they are stable within the cell prior to infection. In an alternative embodiment, the ancillary heterologous nucleic acid(s) can be under the control of an inducible promoter. Inducible promoters include the metallothionein promoter (e.g., the zinc-inducible sheep metallothionine promoter), the tetracycline-on and the tetracycline-off promoters (Gossen et al. (1992) Proc. Natl. Acad. Sci., 89:5547-5551; Gossen et al. (1995) Science 268:1766-1769; Harvey et al. (1998) Curr. Opin. Chem. Biol., 2:512-518) and the heat shock protein 70 promoter. Therefore, in a particular embodiment, a cell that contains the ancillary heterologous nucleic acid(s) (e.g., in a plasmid) under the control of an inducible promoter are treated with an agent that induces their expression prior to placing the defective viral vector and the defective helper virus into the cell.

A defective helper vector can be prepared by deleting one or more genes that are required for viral propagation, such as genes that are required for replication and/or packaging. In the Examples below, an HSV virus having a deletion in both copies of the ICP4 gene was used. A cassette containing what will be the helper heterologous nucleic acids can then be inserted into the defective helper vector. As disclosed below, the 5 adenovirus (Ad) genes: E1A, E1B, E2a, E4orf6, and VAI RNA were inserted into the HSV helper vector missing the ICP4 gene. The resulting hybrid defective helper virus (e.g., the HSV/Ad helper vector described below) can be replicated (and where appropriate packaged) when re-infected into permissive cells which express the exogenous gene product.

The permissive cells are also co-infected with the ultimate product, a defective viral vector. A defective AAV vector and a "gutless" adenoviral vector are exemplified below. This gutless adenoviral vector contained adenovirus termini (harboring origins of DNA replication) and a packaging signal, but no other adenovirus genes. Other suitable defective viral vectors include but are not limited to cytomegalovirus (CMV), simian vacuolating virus 40 (SV40), human papillomavirus (HPV), Hepatitis B virus, JC papovaviridae virus and Esptein Bar Virus (EBV).

After the co-infection a mixed production stock of packaged defective viral vector and defective helper vector is produced. This production stock can be repeatedly re-infected into fresh permissive cells, readily yielding increasingly larger quantities of the mixed production stock. When the titer is optimized to a desired value, packaged defective viral vector free of defective helper vector can be produced by passing the production stock through the non-permissive cells.

The helper-free defective viral vectors are then isolated from the non-permissive cells. Any of a number of methods can be used. For example, the cells can be subjected to sonication and/or to freeze-thaw protocols. The cell debris then can be removed by centrifugation for example. Additional purification of the helper-free defective viral vectors from cell debris and cellular components can be performed such as through the use of an affinity column (e.g., using an antibody specific for a coat protein), size exclusion columns, including spin columns, size exclusion membranes with dialysis, ammonium sulfate fractionation/precipitation, and cesium chloride gradients.

When sequences from the same virus are employed in the defective helper virus and the plasmid, e.g., adenoviral vector, it is preferred that a large insertion of "stuffer" DNA be inserted into the viral (e.g., adenovirus) sequences of the EBV plasmid of the cell lines. The use of stuffer DNA in a plasmid prevents the plasmid DNA from being packaged because the addition of stuffer DNA to the viral DNA of the plasmid makes it too large to be packaged. For example, since adenovirus can maximally package up to 105% of its genome size of 35 kb, an addition of greater than about 2 kb prevents the DNA from being packaged into an adenoviral particle. Although production of wild-type adenovirus through recombination should be prevented by the preferred absence of complementary sequences between the defective helper vector and the cell line, the insertion of the stuffer sequence adds an additional safety measure since any unlikely recombinant would be too large to package.

Preferably the defective helper vector is packaged, i.e., a viral particle that comprises helper heterologous nucleic acids (e.g., the HSV/Ad helper vector). However, in an alternative embodiment, the helper heterologous nucleic acids can be inserted into a replication defective viral amplicon (an HSV/Ad amplicon) and this amplicon can then be packaged in a permissive cell with the aid of a replication defective helper virus, e.g., an ICP4-deleted HSV, into a viral coat (e.g., the HSV viral protein coat) forming a viral particle. In one embodiment of this type, the permissive cell does not contain any heterologous nucleic acids besides the exogenous nucleic acid required for the replication of the viral amplicon. The resulting mixture of defective viral amplicon and defective helper vector (e.g., HSV/Ad amplicon-defective helper vector) can be placed (e.g., re-infected) into a fresh permissive cell allowing the amplification of the mixture. As is readily apparent, when a mixture of a viral amplicon and defective helper vector is employed, the helper heterologous nucleic acids can be distributed in any of the possible permutations between the defective helper vector and the defective viral amplicon. All of such permutations are included by the present invention.

In an alternative embodiment the ancillary heterologous nucleic acid sequences contained within the cell line (e.g., via a plasmid as exemplified below) can alternatively be supplied by a second amplicon, which could be packaged as part of the helper mix along with the amplicon harboring the helper heterologous nucleic acid sequences. In yet another embodiment, the permissive cell line could minimally contain a lone viral nucleic acid, i.e., an exogenous nucleic acid required for packaging the defective helper virus, e.g., the HSV ICP4 as exemplified below, which would be absent in the corresponding non-permissive cell line. In this case all of the other requisite heterologous nucleic acids could be inserted into a single amplicon, without any viral packaging signals or origins of replication, and the amplicon could be packaged into a "helper" amplicon which could autonomously support packaging of a defective viral vector.

The present invention uniquely enables the large scale production of vector stocks for any selected defective viral vector. Preferably the defective viral vector is a defective DNA viral vector that does not encode a viral protein but comprises recognition signals for replication and packaging mediated by exogenous viral genes. In one embodiment of the invention, the defective viral vector is a circular AAV-derived vector comprising one or more 61 bp element(s) having the sequence of SEQ ID NO:16.

When the vectors of the present invention are employed for gene therapy, the recipient may be in need of gene therapy due to one or more mutations in the regulatory region and/or the coding sequence of one or more genes. Therefore, DNA delivered to that individual may be considered heterologous even though it is identical to a gene native to that individual's species, provided it differs in the regulatory or coding region from the cognate gene of the individual to whom it is delivered, and therefore encodes a different gene product or is expressed to a different degree and/or in different cells, under at least some conditions.

cAAVs

In addition to the commonly accepted self-priming strand displacement model described above, another AAV replication pathway was recently identified which is characterized by the assembly of circular duplex monomer genomes (cAAV) (Musatov et al. (2000) Virology 275:411-432). These circular species may constitute as much as 10% of monomer duplex intermediates of both wild-type and recombinant AAV, although on occasion these structures are barely detectable. The circularization point (so-called the "TRT domain") of cAAV contains a single copy of the ITR flanked by two D-elements (D-A'-B'-B-C'-C-A-D). cAAV can either replicate along the accepted strand-displacement pathway following resolution of the TRT domain (defined here as a "conventional pathway") or by a mechanism that preserves the integrity of the circular conformation ("alternative pathway").

The requirement of cAAV for cis-acting elements for replication, the relationship between the two pathways, and the biological significance of the circular duplex intermediates were investigated in experiments described below (Example 5). A series of cAAV plasmids containing various deletions in the TRT domain were constructed, and analyzed the effect of these alterations on AAV replication and packaging in cell culture. These experiments led to a novel discovery regarding the identity and characterization of a minimal ITR sequence necessary and sufficient to support cAAV replication, e.g., the 61 bp AD sequence (SEQ ID NO:16). Interestingly, a small internal palindrome (BB') known to comprise an additional Rep-binding element (RBE') necessary for optimal Rep-ITR interaction (Brister et al. (2000, ) J. Virol. 74:7762-7771) does not contribute to the efficiency of cAAV replication, while the trs is an essential cis-acting element. Furthermore, rAAV harboring only the AD domain replicate exclusively in a circular form and no linear duplex intermediates are assembled.

The experiments below are the first evidence that the conventional and alternative pathways of AAV replication are indeed independent and can be completely separated. Further, as shown below, these studies revealed that cAAV genomes with the AD domain are efficient templates for the packaging of ssDNA as well.

Example 5 below describes the role of a cis-acting element that directs circular Adeno-associated virus (cAAV) replication and packaging. Replication of cAAV constructs containing various deletions in the TRT domain were assayed using two different models of rAAV propagation in cell culture. Hirt DNA samples digested with DpnI or DpnI and XbaI were resolved on a neutral agarose gel. These enzymes would unambiguously distinguish between different replicative intermediates as well as input plasmid DNA. DpnI selectively cleaves methylated input plasmid but is inactive against templates that have undergone at least one round of replication in mammalian cells. As shown in FIG. 2, digestion of unreplicated plasmid with DpnI followed by hybridization with a CMV promoter probe is expected to reveal a band of approximately 1.2 kb. When digested with XbaI, replicative form monomers (Rfm) and tail-to-tail dimers (RFd, T-T) should release 0.9-kb and 0.8-kb fragments for extended and closed ends, respectively, while head-to-head dimers (RFd, H-H) are expected to liberate a 1.5-kb band. Finally, circular AAV structures are predicted to produce a unique 3.3-3.5-kb fragment following XbaI digestion, depending upon the size of the ITR element. As indicated above, DpnI should not cleave any of the replicative forms.

Figure 3:
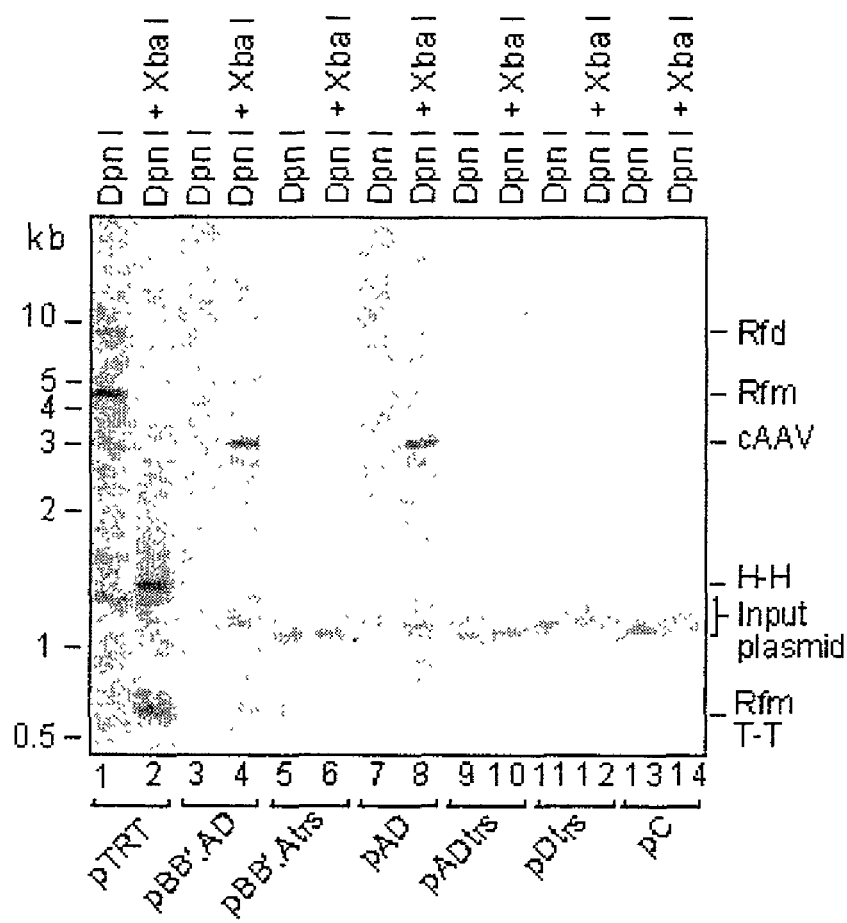
Figure 4:
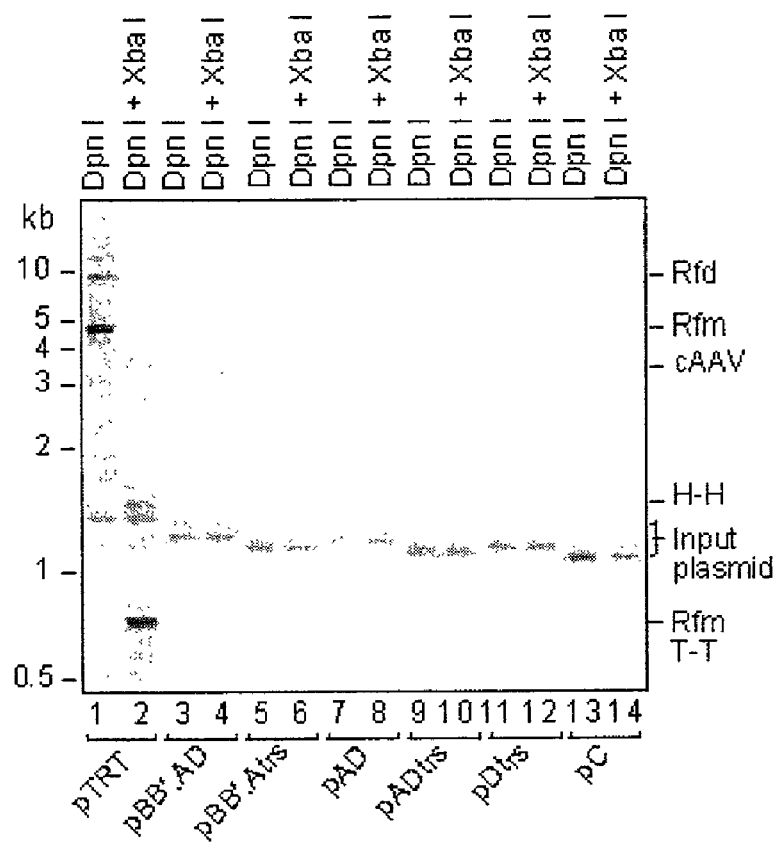

Southern blots presented in FIGS. 3 and 4 show that DpnI-digested samples for pTRT had a banding profile that is characteristic for AAV lytic replication, including linear duplex Rfm and Rfd (FIG. 3, lane 1). It should be noted, that cAAV species are not always detected during replication of pTRT in a helper-free system (FIG. 3, lane 2) but can be readily recognized when adenovirus is used to provide helper functions (FIG. 4, lane 2) or when a conventional cis-plasmid is used as a template. When the CC' hairpin as well as a second copy of the AD sequence were removed (pBB'.AD), dramatic changes in the replication profile were observed. No linear duplex intermediates were clearly detected (FIGS. 3 and 4, lane 3); instead the plasmid replicated apparently exclusively in a circular form as evidenced by release of the unique 3.3-kb fragment following XbaI digestion (FIGS. 3 and 4, lane 4). The absence of intact circular forms samples cleaved with DpnI alone is likely due to cAAV migration in multiple conformations (e.g. supercoiled and relaxed), which would limit concentration at any one location in a gel. Equal intensities of the 1.2-kb bands liberated by DpnI from input DNA in each lane suggests that these findings are not a result of variabilities in transfection efficiency, sample loading or transfer during blotting.

Experiments investigated whether the D-element was essential for the alternative replication pathway. pBB'.Atrs lacks 18 bp of this 20-bp sequence while retains 2 bp that complement the trs (FIG. 1). As can be seen in FIGS. 3 and 4, lanes 5 and 6, no DpnI-resistant material was detected indicating that the D-element is a critical region in the origin of cAAV replication. To more precisely localize the minimal 5' end of the ITR sequence, the BB' hairpin in pAD was removed. This small internal palindrome has been shown to comprise a cis-acting element (RBE') essential for origin function of the ITR (Brister et al. (2000) J. Virol. 74:7762-7771). Surprisingly, this alteration did not impair cAAV replication (lane 8). However, deletion of the D-element from this construct (pAtrs) completely abolished replication, an observation consistent with the previous finding of the importance of this domain (lanes 9 and 10).

The involvement of the A-sequence in this pathway was addressed. Construct pDtrs retains the complete D-element and 4 bp of the A-sequence that complement the trs, but lacks the rest of this element including the Rbs (FIG. 1). As shown in FIGS. 3 and 4, lanes 11 and 12, this mutation was deleterious for cAAV replication. Vector pC, which does not contain any AAV sequence, was included as a negative control (lanes 13 and 14). Thus, cis-elements required for replication of cAAV can be assigned to a single AD domain of the ITR. The experiments also revealed that that the "conventional" and "alternative" pathways are indeed independent and can be completely separated.

To determine whether trs is necessary for cAAV replication, two point mutations were introduced into the trs. Nicking normally occurs between the TT residues in the trs, and these were substituted with two CC residues (FIG. 1). This alteration is expected to completely block endonuclease reaction mediated by Rep (Brister et al. (1999) J. Virol. 73:9325-36). When assayed for replication in 293 cells, this construct failed to produce DpnI-resistant species compared to a control pAD plasmid. Equal intensities of the 1.2-kb bands released after DpnI cleavage serves as a control for equal transfection efficiency and gel loading in this experiment. Thus, trs is an essential cis-element of the alternative pathway of AAV replication.

The extent of plasmid DNA replication in mammalian cells can be easily assayed by resistance to DpnI and MboI. DpnI is active only towards templates that have both adenosines methylated in the GATC recognition sequence. In contrast, MboI cleaves the same site only if both strands are unmethylated. Since such methylation is performed only in dam$^+$ bacteria but not mammalian cells, sensitivity to DpnI and resistance to MboI indicate that the plasmid has not replicated. Following one round of DNA synthesis, the template becomes hemimethylated and is DpnI- and MboI-resistant. After the second round of replication, both DNA strands will be unmethylated, and the plasmid will be DpnI-resistant and MboI-sensitive.

Figure 5:
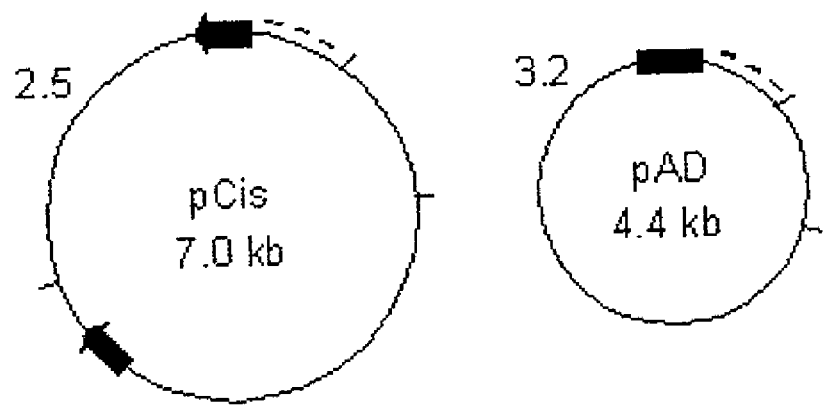
FIGS. 5-6. Comparison of replication of pCis and pAD.
Figure 6:
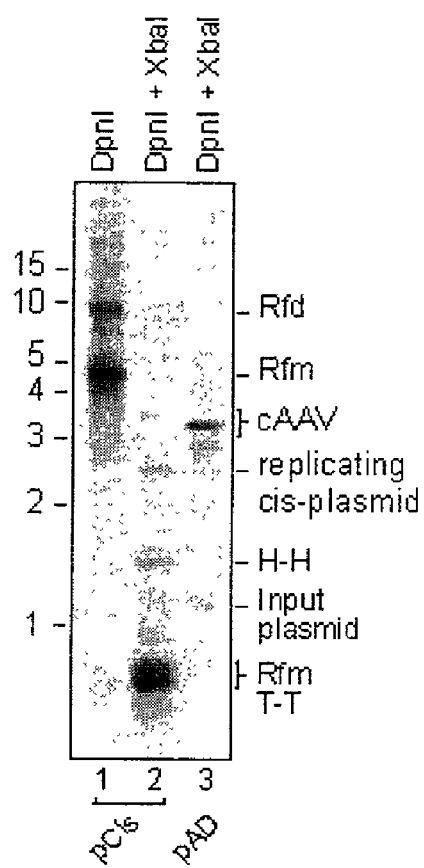

The pAD replication products from the experiment described in FIG. 3 were analyzed to determine whether cAAVs undergo more than one round of DNA synthesis during replication. Hirt DNA samples were digested with XbaI to release a 3.2-kb band unique for cAAV and then with DpnI or DpnI and MboI. All DpnI-resistant species were also MboI-sensitive (results not shown). Indeed, a 3.2-kb band corresponding in mobility to replicated pAD was completely converted to a 1.2-kb fragment positioned between two DpnI/MboI sites. This finding establishes that pAD replication products are the result of more that one round of DNA synthesis.

cAAV replication using pTRT as a template was found to be less efficient compared to conventional cis-plasmids, which harbor a rAAV genome with two complete ITRs separated by a stuffer sequence. To ensure that these findings were not limited to a particular set of constructs, but rather relevant to a mechanism of AAV replication in general, a regular cis-plasmid was included as a control. This vector (pCis) contains the same non-AAV sequence as pAD, and has two intact ITRs derived from psub201 (33) separated by a 2.3-kb stuffer (FIG. 5). As shown in FIG. 6, cAAVs were assembled far more efficiently during pCis propagation than during replication of pTRT (compare FIG. 6, lane 2 and FIG. 3, lane 2). Similar intensities of the 1.2-kb bands released after DpnI cleavage of input plasmid serve as a control for equal transfection efficiency and gel loading in this experiment (compare lanes 2 and 3 in FIG. 6). Densitometry analysis of this blot established that cAAV intermediates constitute approximately 10% of linear duplex structures (Rfm). This observation confirms previous report that cAAV is reproducibly identified during AAV replication (Musatov et al. (2000) Virology 27 5:411-432). Equally important, this experiment revealed that a substitution of ITRs with a single AD domain enhances replication of cAAV (compare lanes 2 and 3) while eliminates generation of linear forms. This effect may be underestimated given the fact that pAD contains only one copy of this element while pCis has two AD copies in opposite orientations. Thus, blocking of the primary replication pathway leads to an increase in the efficiency of the alternative pathway of replication.

To address the issue of size constraints, the replication of two other constructs of larger size, 2n (9 kb) and 3n (13.6 kb) was assayed. The plasmids were transfected into 293 cells in equimolar amounts along with a full complement of helper functions. Hirt DNA samples were digested with a single-cutting enzyme, resolved on an agarose gel, and the resulting blots were hybridized with an EGFP-specific probe. Results (not shown) show that replication of 2n was significantly impaired compared to pAD, and there was no detectable 3n replication. In a separate experiment, the replication of a plasmid of a smaller size (2.3 kb) was found to be even more efficient than that of pAD (data not shown). These findings indicate that though replication of cAAV is not limited to genomes of wt size, it becomes inefficient as the size of a template increases.

During replication of cAAV constructs in our experiments, a restriction endonuclease-resistant smear was always observed on Southern blots. The smear could at least in part be attributed to ssDNA that is known to migrate abnormally in a neutral agarose gel. This finding prompted the investigation of packaging of the cAAV constructs. All of the plasmids have a size of approximately 4.4-4.6 kb so they could be packaged without rescue if such rescue-independent encapsidation is possible. Production of infectious virions was directly assayed on 293 cells by limiting dilution of crude cell lysates. These lysates were prepared from a portion of the same samples that were used for the replication assay described below. This permits conformation of equal plasmid transfection efficiencies of the plasmids by Southern blotting and allows us to correlate replication profiles and packaging.

We were surprised to discover relatively high numbers of EGFP-positive cells for some samples 24 h post-infection (Table 3). There was a direct correlation between efficient replication of cAAV and packaging. This is best illustrated by comparing replication profiles of pTRT, pBB'.AD and pAD (FIG. 3) and corresponding infectious particle titers (Table 3). No EGFP-positive cells were found for the other constructs including the negative control. For clarity, we will use an "AAV" prefix to denote virus, while prefix "p" to refer to a corresponding plasmid, e.g. AAV.AD is a virus produced by pAD. Virtually no difference between AAV.BB'.AD and AAV.AD titers was found, an observation consistent with a similar efficiency of replication of the corresponding plasmids (compare lanes 4 and 8 in FIG. 3). This once again establishes that the BB' palindrome is dispensable for AAV replication once a switch to a different replication pathway has occurred.

To examine the structure of packaged AAV.AD genomes, crude lysates were extensively digested with DNase I, virion DNA was then extracted, resolved on a neutral agarose gel and analyzed using Southern blotting. A 2.2-kb band corresponding in size to ssDNA was released from AAV.AD virions (not shown). AAV.TRT was included as a positive control. There was a slightly higher intensity of AAV.AD ssDNA band compared to that of AAV.TRT, an observation consistent with a higher yield of AAV.AD infectious virions compared to the control (Table 3). Thus, the result established that virions produced by pAD indeed contain full-length ssDNA.

Since AAV.AD contains only a truncated single copy of ITR, the ability of this domain to target site-specific recombination was tested. For this purpose, the method of Palombo et al. (1998) J. Virol. 72:5025-50334 was used which is based on PCR amplification of AAV-AAVS1 junctions from genomic DNA. To distinguish between unidirectional and bidirectional integration, sets of nested primers were used for both 5' and 3' ends of the vector sequence. Infections were performed in 293 cells in the presence or absence of Rep provided by transient plasmid transfection. AAV.TRT was included as a positive control.

Figure 7:
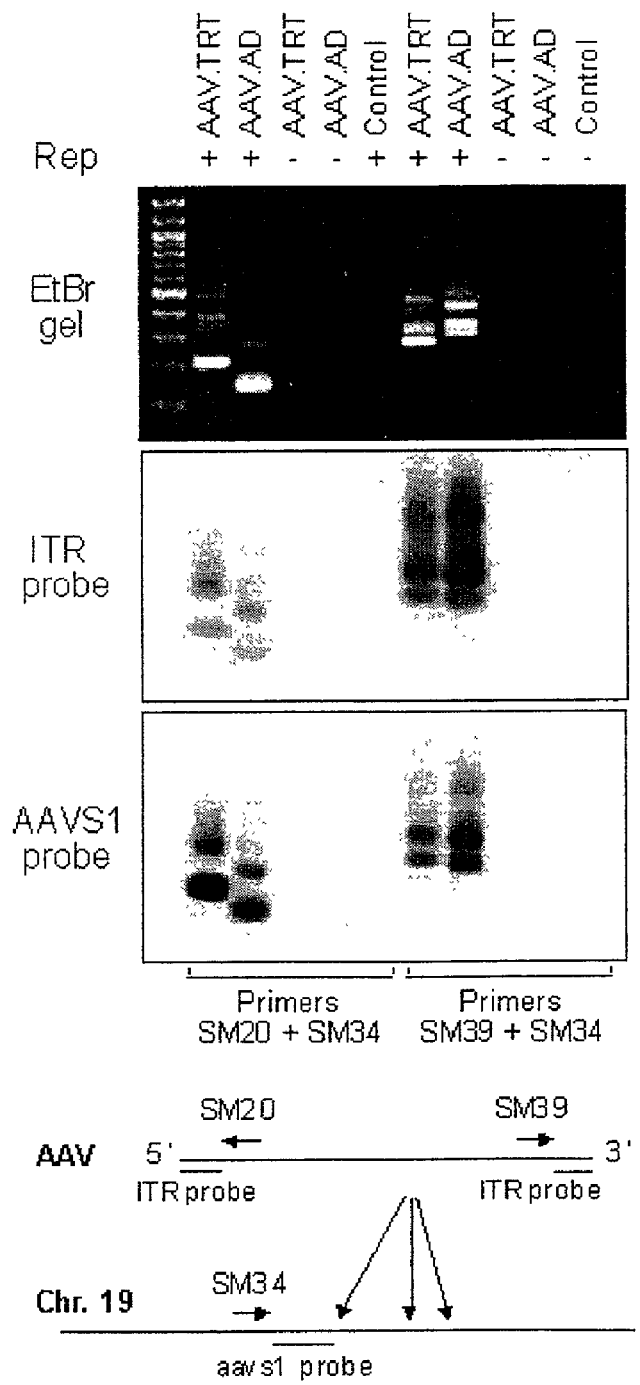
FIG. 7. Site-specific integration of AAV.AD. 293 cells were infected with AAV.AD or AAV.TRT (positive control) in the presence or absence of Rep. Genomic DNA was extracted 72-h post-infection and subjected to nested PCR. Mock-infected cells were included as a negative control. PCR products were analyzed on an ethidium bromide gel (top) and duplicate southern blots (bottom), which were analyzed using $^{32}$P-labeled ITR-specific or AAVS 1-specific probes. A 100-bp ladder was loaded into the first lane. Viruses used for the assay are indicated along the top of the gel. The AAV genome, AAVS 1 integration site, position of primers and probes are schematically represented at bottom.
Figure 8:
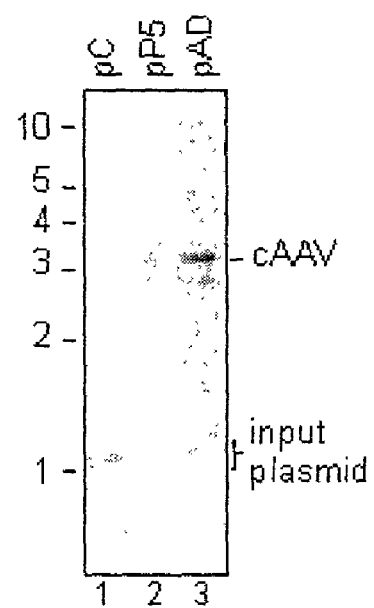
FIG. 8. Comparison of pP5 and pAD replication. pP5 and pAD were assayed for replication as described in the legend of FIG. 3. pC was included as a negative control. Note the absence of linear duplex intermediates in lanes 1 and 2. Replicating cAAV and input plasmids are indicated. 1-kb size markers are shown to the left of the blot.

As shown in FIG. 7, specific DNA bands were amplified from 293 cells infected with both AAV.TRT and AAV.AD. The product appears as a smear with multiple bands, which probably reflects the heterogeneity of junction species in a population of transduced cells. Note, that no signal was detected in mock-infected cells or cells infected with viruses in the absence of Rep. To confirm the nature of the amplified product, duplicate blots were hybridized with ITR or AAVS 1 specific probes. There is a good correspondence of the hybridization signals between these two blots, further suggesting that the fragments indeed include both AAV and AAVS1 sequences. Equally important, this experiment revealed the ability of AAV.AD genome to integrate in either orientation despite the polarity of the AD domain in a vector plasmid. The PCR products containing both 5' and 3' termini of AAV.AD were also subcloned into pCR2.1 (Invitrogen) and sequenced. While the analysis revealed the presence of both AAVS 1 and AAV.AD sequences in all the clones analyzed, extensive deletions both within the AD domain and the integration site were detected (data not shown). This finding, however, is consistent with other reports on rAAV integration marked by rearrangements of an integration site and viral termini (Kotin et al. (1992) EMBO J. 11:5071-5078; Surosky et al. (1997) J. Virol. 71:7951-7959). Taken together, these results establish that a single AD domain in the context of a virion genome serves as an efficient signal for Rep-mediated site-specific recombination.

Having identified a minimal ITR sequence that encompasses Rbs, trs and the D-element as an origin of a novel pathway of AAV replication, other sequences were examined for such elements. One of the best-characterized Rep-binding elements is mapped to the AAV endogenous P5 promoter. The P5 promoter has been found to be involved in amplification of integrated Rep-Cap sequences in HeLa cells (Chadeuf et al. (2000) J. Gene Med. 2:260-268; Nony et al. (2001) J. Virol. 75:9991-9994; Tessier et al. (2001) J. Virol. 75:375-383) as well as to enhance the propagation of wtAAV itself (Tullis et al. (2000) J. Virol. 75:11511-11521). Considering high homology between the AD domain and the P5 promoter, we speculated that all these phenomena are examples of the alternative replication pathway described here. To test this hypothesis, plasmid pP5 was created by substituting the 61-bp AD domain in pAD with an 86-bp Nla III fragment from psub201 (Samulski et al. (1987) J. Virol. 61:3096-3101) containing the P5 promoter (nucleotides 238-324 of AAV-2). This element was inserted in a "direct" orientation, i.e. the same orientation as in psub201. pP5, pC (a negative control) and pAD (a positive control) were transfected into 293 cells along with a full complement of helper functions and then assayed for replication and packaging.

We were surprised to discover that the replication profile of pP5 was virtually indistinguishable from that of pAD (results not shown). In fact, both plasmids replicated exclusively in a circular form and no linear duplex intermediates were detected. Even more remarkable, pP5 was a template for packaging as well, albeit approximately 5 fold less efficiently than pAD. This can be illustrated by comparing functional AAV titers produced by pAD and pP5 (Table 4). Note that both vectors demonstrated a similar level of increase in transduction efficiency by a secondary infection with adenovirus. In summary, the results establish that cis signals for cAAV replication and packaging are not limited to the AD domain of the ITR, but may include other homologous sequences, e.g. the P5 promoter.

Gene Therapy

The helper-free defective viral vectors of the present invention can be used to transfer genetic information to any cell, and preferably human cells. However, cells of other mammals, such as rodents, e.g., mice, rats, rabbits, hamsters and guinea pigs; farm animals e.g., sheep, goats, pigs, horses and cows; domestic pets such as cats and dogs, higher primates such as monkeys, and the great apes such baboons, chimpanzees and gorillas can also be cell targets.

The helper-free defective viral vectors of the present invention can comprise any heterologous nucleic acid of interest preferably those encoding proteins. Indeed, any protein can be encoded by a nucleic acid of the defective viral vector. A short list of a few of these proteins and their roles in particular conditions and/diseases are included in Table 1 below. However, this listing should in no way limit the general methodology of the present invention which provides helper-free defective viral vectors that can comprise any nucleic acid of choice. Furthermore, the helper-free defective viral vectors of the present invention can also encode multiple proteins and/or be used in a regimen in which the individual defective viral vectors encode different proteins.

In one particular example a helper-free defective viral vector of the present invention is employed to transduce neurons in vivo to treat Parkinson's disease. In this case, the heterologous nucleic acid encoded by the helper-free defective viral vector can be human tyrosine hydroxylase. Therefore, in one embodiment of the present invention, the helper-free defective viral vectors of the present invention are used to deliver the gene for tyrosine hydroxylase (Genbank HUMTHX, Accession No. M17589) to brain cells. Preferably, a nucleic acid encoding aromatic amino-acid decarboxylase (Genbank HUMDDC, Accession No. M76180) is delivered in conjunction with the nucleic acid encoding tyrosine hydroxylase. As described previously (U.S. Pat. No. 6,180,613, Issued Jan. 30, 2001, the subject matter of which is hereby incorporated by reference in its entirety) transducing striatal cells with a viral vector to express dopamine synthesizing enzymes may be purely a palliative approach to treating Parkinson's disease, and the underlying disease process will continue unabated. Therefore, helper-free defective viral vectors of the present invention also can be employed that express "neuroprotective or neurotrophic" factors to prevent further degeneration of dopaminergic neurons and promote regeneration. This approach can include the most specific neurotrophic factor for mesencephalic dopaminergic neurons identified to date, glial-derived neurotrophic factor (GDNF). Other neurotrophic factors of the NGF family have previously been expressed from HSV-1 vectors and shown to have neuroprotective effects. These neurotrophic factors appear to act through tyrosine kinase receptors to prevent apoptosis. As the proto-oncogene bcl-2 can prevent neuronal apoptosis in vitro, helper-free defective viral vectors of the present invention that express bcl-2 can also be used to prevent apoptosis in vivo.

Therefore, gene therapy for Parkinson's disease can further involve the delivery of helper-free defective viral vectors of the present invention containing nucleic acids GDNF (Genbank HUMGDNF02; Accession No. L19063), brain-derived neurotrophic factor (BDNF), nerve growth factor (NGF) (EMBL HSNGF2; Accession No. X53655, and/or other members of the neurotrophin factor family including neurotrophin (NT)-3 (Genbank HUMBDNF; Accession No. M37762) and NT-4 (Genbank HUMPPNT4P; Accession No. M86528) as well as additional proteins.

In any case, heterologous nucleic acids are preferably operatively linked to an expression control sequence (e.g., an early cytomegalus virus). The present invention can be performed with any such expression control sequence, but is preferably performed with an expression control sequence that is obtained from or is a tissue specific promoter (see U.S. Patent No:6,040,172, Issued Mar. 21, 2000, the subject matter of which is hereby incorporated by reference in its entirety). Such promoters include the preproenkephalin promoter or the glial fibrillary acidic protein promoter when a nervous system cell is the target. Other promoters include, but are not limited to, the SV40 early promoter region (Benoist et al. (1981) Nature, 290:304-310), the promoter contained in the 3' long terminal repeat of Rous sarcoma virus (Yamamoto et al. (1980) Cell, 22:787-797), the herpes thymidine kinase promoter (Wagner et al. (1981) Proc. Natl. Acad. Sci. U.S.A. 78:1441-1445), the regulatory sequences of the metallothionein gene (Brinster et al. (1982) Nature 296:39-42); prokaryotic expression vectors such as the β-lactamase promoter (Villa-Kamaroff et al. (1978) Proc. Natl. Acad. Sci. U.S.A. 75:3727-3731), or the tac promoter (DeBoer et al. (1983) Proc. Natl. Acad. Sci. U.S.A. 80:21-25); see also "Useful Proteins from Recombinant Bacteria", Scientific American (1980) 242:74-94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al. (1984) Cell 38:639-646; Ornitz et al. (1986) Cold Spring Harbor Symp. Quant. Biol. 50:399-409; MacDonald (1987) Hepatology 7:425-515); insulin gene control region which is active in pancreatic beta cells (Hanahan (1985) Nature 315: 115-122), immunoglobulin gene control region which is active in lymphoid cells (Grosschedl et al. (1984) Cell 38:647-658; Adames et al. (1985) Nature 318:533-538; Alexander et al. (1987) Mol. Cell. Biol. 7:1436-1444), mouse mammary tumor virus control region which is active in testicular, breast, lymphoid and mast cells (Leder et al. Cell (1986) 45:485-495), albumin gene control region which is active in liver (Pinkert et al. (1987) Genes and Devel. 1:268-276), alpha-fetoprotein gene control region which is active in liver (Krumlauf et al. (1985) Mol. Cell. Biol., 5:1639-1648;

Hammer et al. (1987) Science 235:53-58), alpha 1-antitrypsin gene control region which is active in the liver (Kelsey et al. (1987) Genes and Devel. 1:161-171), beta-globin gene control region which is active in myeloid cells (Mogram et al. (1985) Nature 315:338-340; Kollias et al. (1986) Cell 46:89-94), myelin basic protein gene control region which is active in oligodendrocyte cells in the brain (Readhead et al. (1987) Cell 48:703-712), myosin light chain-2 gene control region which is active in skeletal muscle (Sani (1985) Nature 314: 283-286), and gonadotropic releasing hormone gene control region which is active in the hypothalamus (Mason et al. (1986) Science 234:1372-1378).

In addition, the dihydrofolate reductase (DHFR) promoter, as exemplified in pED, see Kaufman (1991) Current Protocols in Molecular Biology, 16.12 or a glutamine synthetase and/or methionine sulfoximine promoter, such as pEE14 sold by Celltech can also be employed by the present invention.

In one embodiment, the expression control sequence is a genetic regulatory sequence from an inducible promoter. Novel and general methodology for identifying inducible promoter elements (including tissue-specific promoters) which are responsive to a pulsatile electromagnetic stimulus and/or a random peptide stimulus has been described in U.S. S No. 60/292,604, filed May 22, 2001, the subject matter of which is hereby specifically incorporated by reference in its entirety. All such genetic regulatory sequences can be employed by the helper-free defective viral vectors of the present invention either alone or in conjunction with other expression control sequences.

The helper-free defective viral vectors of the present invention can be delivered in vitro, ex vivo and in vivo. As previously exemplified the delivery can be performed by stereotaxic injection (U.S. Pat. No. 6,180,613, Issued Jan. 30, 2001, the subject matter of which is hereby incorporated by reference in its entirety) into the brain for example, or via a guide catheter (U.S. Pat. No. 6,162,796, Issued Dec. 19, 2000, the subject matter of which is hereby incorporated by reference in its entirety) to an artery to treat the heart. In addition, the helper-free defective viral vectors of the present invention may also be delivered intravenously, topically, intracerebroventricularly and/or intrathecally, for specific applications. Additional routes of administration can be local application of the vector under direct visualization, e.g. superficial cortical application, or other non-stereotactic applications.

For targeting the vector to a particular type of cell, it may be necessary to associate the vector with a homing agent that binds specifically to a surface receptor of the cell. Thus, the vector may be conjugated to a ligand (e.g., enkephalin) for which certain nervous system cells have receptors, or a surface specific antibody. The conjugation may be covalent, e.g., a crosslinking agent such as glutaraldehyde, or noncovalent, e.g., the binding of an avidinated ligand to a biotinylated vector.

In addition, the helper-free defective viral vectors of the present invention can be delivered ex vivo, as exemplified by Anderson et al. (U.S. Pat. No. 5,399,346, Issued Mar. 21, 1995, the subject matter of which is hereby incorporated by reference in its entirety).

TABLE 1

PROTEINS INVOLVED IN SPECIFIED CONDITIONS AND DISEASES

| GENETIC DEFECTS | DISEASE/SYMPTOM |
| --- | --- |
| adenosine deaminase | severe combined immunodeficiency disea |
| alpha, - antitrypsin | pulmonary emphysema |

TABLE 1-continued

PROTEINS INVOLVED IN SPECIFIED CONDITIONS AND DISEASES

| GENETIC DEFECTS | DISEASE/SYMPTOM |
| --- | --- |
| 5-alpha reductase | male pseudohemaphroditism |
| 17 - alpha reductase | male pseudohemaphroditism |
| p53 or ARF-P19 | proteins linked to cancer |
| insulin | insulin-dependent diabetes |
| sickle cell anemia | B-globin |
| hypoxanthine guanine phosphoribosyl-transferase | Lesh-Nyhan Syndrone |
| omithine transcarbamolase | Fatal to newborn males |
| tyrosine hydroxylase | Parkinson's disease |
| phenylalanine hydroxylase | Phenylketonuria |
| Dralassemia | x- or B-globin |
| AT Page 7 A | Menkes' syndrome |
| AT Page 7B | Wilson Disease |
| hexosamindase A | Tay-Sachs Disease |
| acid cholesterylester hydrolase | Wolmon Disease |

Ribozymes and Antisense

In one embodiment of the invention, the helper-free defective viral vector of the invention provides an antisense nucleic acid or a ribozyme. Antisense nucleic acids are DNA or RNA molecules that are complementary to at least a portion of a specific mRNA molecule (See Weintraub (1990) Sci. Amer. 262:40-46; Marcus-Sekura (1987) Nucl. Acid Res. 15: 5749-5763; Marcus-Sekura (1988) Anal. Biochem. 172:289-295; Brysch et al. (1994) Cell Mol. Neurobiol. 14:557-568). Preferably, the antisense molecule employed is complementary to a substantial portion of the mRNA. In the cell, the antisense molecule hybridizes to that mRNA, forming a double stranded molecule. The cell does not translate an mRNA in this double-stranded form. Therefore, antisense nucleic acids interfere with the expression of mRNA into protein. Preferably a DNA antisense nucleic acid is employed since such an RNA/DNA duplex is a preferred substrate for RNase H. Oligomers of greater than about fifteen nucleotides and molecules that hybridize to the AUG initiation codon will be particularly efficient. Antisense methods have been used to inhibit the expression of many genes in vitro (Marcus-Sekura (1988) Anal. Biochem. 172:289-295; Hambor et al. (1988) Proc. Natl. Acad. Sci. U.S.A. 85:4010-4014) and in situ (Arima et al. (1998) Antisense Nucl. Acid Drug Dev. 8:319-327; Hou et al. (1998) Antisense Nucl. Acid Drug Dev. 8:295-308).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these ribozymes, researchers have been able to engineer molecules that recognize specific nucleotide sequences in an RNA molecule and cleave it (Cech (1988) JAMA, 260:3030-3034; Cech (1989) Biochem. Intl. 18:7-14). Because they are sequence-specific, only mRNAs with particular sequences are inactivated.

Investigators have identified two types of ribozymes, Tetrahymena-type and "hammerhead"-type (Haselhoff et al. (1988) Nature 334:585-591). Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

When it is desired to place a specific antisense nucleic acid or ribozyme into a cell, tissue or animal subject, the heterologous nucleic of interest can be that specific antisense nucleic acid or ribozyme. Therefore, such an antisense nucleic acid or ribozyme can be included in a helper free defective viral vector of the present invention. Such a helper free defective viral vector can be used to specifically prevent a cell, tissue or animal subject from expressing a particular protein. The cell, tissue or non-human animal subject can then be used to determine the role of that protein.

In one embodiment, a protein involved in a disease state is selected and the cell, tissue or non-human animal subject can be used in drug screens for identifying compounds that can compensate for the loss of that protein. For example, classical phenylketonuria (PKU) is due to the loss phenylalanine hydroxylase activity. Therefore, compounds and peptidomimetics can be tested using liver cells, liver tissue slices, and/or non-human animal subjects in which a defective viral vector of the present invention containing an antisense nucleic acid or a ribozyme that prevents phanylalanine hydroxylase expression has been administered.

Alternatively, an antisense nucleic acid or ribozyme that prevents the expression of xanthine oxidase can be administered to a patient with gout, since the xanthine oxidase-dependent conversion of xanthine to uric acid is the cause of gout. Similarly, an antisense nucleic acid or ribozyme that prevents the expression of tumor necrosis factor alpha can be administered to a patient in septic shock, or one that has leprosy or tuberculosis. In this case, the fact that the treatment may not lead to 100% inhibition of tumor necrosis factor alpha expression may be beneficial, since most of the detrimental effects due to tumor necrosis factor alpha is due to it over-expression.

EXAMPLES

The following examples are put forth so as to provide those of ordinary skill in the art with a complete disclosure and description of how to make and use the therapeutic methods of the invention and compounds and pharmaceutical compositions, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Production of Helper-Free dAAV Vectors

An hygromycin-sensitive cell line was obtained that expresses the ICP4 gene product. A hygromycin resistant plasmid containing the Epstein-Barr Virus (EBV) origin of replication and the EBNA gene was constructed so as to contain two essential AAV genes, Rep and Cap. This plasmid was then introduced into this cell line. A cell line expressing Rep/Cap and ICP4 was created (i.e., Rep+/Cap+/ICP4+ cells) by selecting cells that were hygromycin resistant. A second cell line was prepared in an analogous manner except the cell line did not express ICP4 (i.e., Rep+/Cap+/ICP4− cells).

Rep/Cap are expressed at low levels in the absence of adenovirus sequences, so they are stable within the cell prior to infection. Both the Rep+/Cap+/ICP4+ cells and the Rep+/Cap+/ICP4− cells were used in the study below.

A defective helper vector was prepared from an HSV virus having a deletion in both copies of the ICP4 gene. Into this viral vector a cassette consisting of 5 adenovirus (Ad) genes: E1A, E1B, E2a, E4orf6, and VAI RNA can be inserted. These are the minimal genes necessary for AAV packaging from an adenovirus vector. The resulting "dHSV/Ad helper vector" produces more defective helper vector when re-infected into cells that express the ICP4 gene product.

A defective AAV vector encoding green fluorescent protein (dAAVGFP), was used to transfect the Rep+/Cap+/ICP4+ cells. After co-infection with the dHSV/Ad helper vector (described above), a mixed production stock of packaged dAAVGFP and dHSV/Ad helper vector was produced. This stock was repeatedly re-infected into the Rep+/Cap+/ICP4+ cells, readily yielding increasingly larger quantities of the mixed production stock. When the titer was optimized, packaged dAAVGFP free of detectable dHSV/Ad helper vector was produced by passing the production stock through the Rep+/Cap+/ICP4− cells. Proof that the helper vectors is removed from the final stock of defective viral vectors can be provided by the inclusion of a marker gene in the helper vector which is not included in the defective viral vector, e.g., luciferase or when it is excluded from the dvv, green fluorescent protein. The expression of the marker protein in the final stock of packaged defective viral vector can then be performed by assaying for the marker protein. In addition, and/or alternatively, Southern blots can be performed, and/or PCR analyses and/or the use of specific antibodies to a protein expressed by the defective helper virus.

Example 2

Production of Helper-Free "Gutless" Ad Vectors

The identical dHSV/Ad helper vector disclosed above, in Example 1 was used with a different cell line for packaging a "gutless" adenovirus (Ad) vector. The gutless Ad vector contains adenovirus termini (harboring origins of DNA replication) and a packaging signal, but no other adenovirus genes.

A cell line was created which contains a subset of the adenovirus genome inserted into the EBV/EBNA plasmid as described in Example 1 above, to create a stable cell line. These adenovirus sequences contain the adenovirus genome with the E1A, E1B, E2a, E4orf6, and VAI RNA sequences deleted. The deletions were performed in a manner which eliminated any overlap with sequences in the dHSV/Ad helper vector and thereby prevent any possible homologous recombination between the two. In order to retain the essential fiber protein in the cell line, the fiber gene was cloned by PCR, and after deletion of the E4 and part of E3 sequences (which necessarily eliminated the fiber gene), the fiber gene sequences were reinserted next to the remaining E3 sequences. These adenoviral sequences were introduced into cells expressing the ICP4 gene, and the resulting cell line was stable since the adenovirus functions within the cell line were not significantly expressed without the 5 genes that had been removed. When these five genes were re-supplied to the cells via the dHSV/Ad helper vector described in Example 1 above, all functions necessary for adenovirus replication and packaging were present within the cell.

A "gutless" adenovirus encoding green fluorescent protein (gutless Ad-GFP), was then co-transfected into the cells. The gutless Ad-GFP was then replicated and packaged along with the dHSV/Ad helper vector. The resulting stock was repeatedly re-infected onto the ICP4/Ad cell line, resulting in increasingly larger mixed stocks in manner identical to that described above for dAAV production of Example 1. As in the process of Example 1, a second cell line was created with the indicated adenoviral sequences, but without ICP4. When infected with the production stock, this cell line yielded pure gutless Ad-GFP without contamination by other adenovirus or HSV/Ad helper vector.

In a variation of this methodology, the additional adenovirus sequences contained within the cell line (see above) can alternatively be supplied by a second amplicon plasmid, which could be packaged as part of the helper mix along with the amplicon harboring the adenovirus early genes. In still another embodiment, all necessary adenovirus sequences can be inserted into a single amplicon, without any adenovirus packaging signals or origins or replication, and this is packaged into a "helper" amplicon which can autonomously support packaging of gutless Ad-GFP or any other "gutless" adenovirus vector. In this embodiment, only ICP4 positive and ICP4 negative cell lines are necessary for generating production and vector stocks, respectively.

Example 3

Construction of Cell Lines

One of the most efficient means of producing recombinant AAV, in theory would be to employ a packaging cell line. Unfortunately, heretofore, development of such a cell line has been limited due to the toxicity of the genes required for AAV replication and virion assembly. As disclosed herein, these genes include the AAV rep and cap genes and the adenovirus transcription units: E1A, E2a, E4orf6 and VA RNA.

The prospects of producing a cell line with a minimal complement of genes appeared to improve with the report that only a subset of these genes (rep, cap, E1 and E4orf6) were sufficient for the generation of high AAV titers (Allen et al. (2000) Mol. Ther. 1(1): 88-95). However, despite extensive efforts, these results could not be confirmed. Indeed, when the rep, cap and E4orf6 coding regions were placed under the control of heterologous promoters, a very poor rAAV titer was obtained (about 0.006 IU/cell).

Importantly, the addition of a plasmid expressing VA RNA resulted in an almost 2-fold increased yield of the vector, whereas the addition of a construct expressing the E2a construct increased the yield over 6 fold. Furthermore, supplementation with both the VA RNA and E2a genes unexpectedly, led to an over 30-fold increase in rAAV vector production. This titer is comparable to titers obtained using standard helper adenovirus or adenovirus helper plasmid systems.

These data demonstrate that to obtain maximal rAAV titers, all of these above-identified adenovirus helper functions should be included, i.e., Rep, Cap, E1A, (and preferably E1B), E2a, E4orf6, and VA RNA. In addition, these results show that the promoters used in conjunction with these coding regions can be freely substituted since these results were obtained with heterologous regulatory sequences rather than the native promoters for the viral genes. Indeed, the promoters listed throughout the specification only serve to exemplify potential alternative choices.

In an attempt to construct a cell line that would harbor all AAV and adenovirus genes necessary for optimal rAAV propagation two plasmids were constructed. In one of them, the bidirectional tet-responsive promoter (Clonetech) drives the expression of cap and E4orf6 coding regions, which are followed by beta-globin and SV40 polyadenylation signals, respectively. This particular cell line also includes the VAI RNA sequence with its native promoter. Incorporation of the hygromycin resistance gene was used to allow selection of stable clones in mammalian cells. The second construct includes the E2a gene placed under the control of the tet-responsive promoter as well as the rep coding sequence driven by the human metallothionein IIA promoter both followed by SV40 polyadenylation signals. Both plasmids were co-transfected into Tet-On (i.e., Tet inducible) 293 cells (Clonetech). Stable clones were established under hygromycin selection. These cells also constitutively express E1 gene products. Upon induction with doxycyclin, these cells express Cap, E4orf6 and E2a, and upon induction with Zn2+ ions these same cells express Rep (because the metallothionein promoter is inducible by Zn2+). Since high concentrations of Rep are known to be both deleterious for optimal AAV propagation, and to be toxic to the host cell, this system allows both the survival of the cell line under uninduced conditions as well as provides the independent control of the intracellular amount of Rep through the use of different concentrations of Zn2+ during vector production. In the absence of the inducers (doxycyclin and Zn2+, as exemplified herein) gene expression from the transgenes is sufficiently low to allow cell survival and growth. It is clear that alternative inducible promoters having alternative inducers can be readily substituted for the promoters and inducers exemplified herein.

To generate the rAAV vector, the cells are initially transfected on a small scale with an AAV vector plasmid carrying an expression cassette. After the first round of packaging, the vector seed stock is then used for further amplification, thus obviating the need for any further plasmid transfections. This 293-based cell line can also grow efficiently in suspension, thereby facilitating large scale vector production using bioreactor-based systems.

Example 4

Circular AAV (cAAV) Vectors

Recombinant cAAV constructs were designed that contain serial deletions in the viral terminal repeats (ITRs) to identify cis-elements responsible for this pathway (Table 2). Rep binding site (Rbs) and terminal resolution site (trs) are underlined.

TABLE 2 cAAV Deletion Mutants

| DELETION | SEQUENCE | |
|---|---|---|
| C'C | CGCCCGGGCAAAGCCCGGGCGT | (SEQ ID NO: 1) |
| B/B' | CGGGCGACCTTTGGTCGCCCGGGGCGTC GGGCGACCTTTGGTCGCCCG | (SEQ ID NO: 2) |

TABLE 2-continued cAAV Deletion Mutants

| DELETION | SEQUENCE | |
|---|---|---|
| A | TTGGCCACTCCCTCTCTGCGCGCTCGCTCGCTCACT-GAGGCGCCTCAGTGAGCGAGCGAGCGCGCAGAGAGGGAGTGGCCAA | (SEQ ID NO: 3) |
| D | AGGAACCCCTAGTGATGGAGCTCCATCACTAGGGGTTCCT | (SEQ ID NO: 4) |
| RBs | GAGCGAGCGAGCGCGC | (SEQ ID NO: 5) |
| trs | CCAACT | (SEQ ID NO: 6) | pTRT is a cAAV that contains a wild-type circularization point (the TRT domain), consisting of a single ITR flanked by two D-sequences. pBB'AD has only one half of the hairpin (BB') followed by single A- and D-elements. pBB'Atrs is similar to the previous construct but has the D-sequence deleted except for the nucleotides that comprise the terminal resolution site (trs).

pAD contains only A- and D-elements. pAtrs is its derivative that has most of the D-element removed while leaving the trs intact. pDtrs contains a single D-sequence and a part of the A-stem to complement trs. pEGFP is a control vector that does not contain any AAV sequences. All plasmids are approximately 4.6 kb and harbor an EGFP expression cassette as well as bacterial ampicillin resistance gene and origin of replication.

To study replication and packaging of these cAAV constructs, the plasmids were transfected into 293 cells along with AAV and adenovirus helper functions (see above). Replication was examined using Dpn I assay of Hirt extracts followed by Southern hybridization. As expected both linear and circular intermediates were observed during pTRT replication, (see Table 3). However, completely unexpectedly, only circular and not linear genomes were detected during the replication of pBB'AD and pAD. Small levels of replication of the other constructs (pBB'Atrs, pAtrs and pDtrs) were not different from that of the control vector pEGFP. These finding demonstrate that the A- and D-domains are the minimal elements required for cAAV replication.

Employing these findings, a recombinant vector was generated which contains the minimal domain sequence, in order to create the first DNA vector based on a linear-replicating virus which can exclusively replicate in a circular fashion. In order to determine possible functional implications of this new vector, virion assembly was assayed by determining functional titers of crude cell lysates. The test was performed on 293 cells in the presence or absence of adenovirus. The cells were scored 24 hours post-infection. As shown in Table 2, pBB'AD and pAD but not the other cAAV constructs were packaged into infectious virions. Importantly, while adenovirus coinfection increased AAV transduction in all cases, the level of enhancement was 8 times lower for AAV.BB'AD and AAV.AD than that for the positive control pTRT. This demonstrates that this new vector provides more efficient transduction without assistance of adenovirus, when compared with conventional AAV vectors.

TABLE 3

Circular AAV Replication and Packaging

| Construct | Linear replication intermediates | Circular replication intermediates | Adenovirus for a functional titer assay | Virus yield, i.u per 35-mm dish | Enhancement of expression by adenovirus |
|---|---|---|---|---|---|
| pTRT | 0 | 0 | 0 | $9.4 \times 10^4$ | 362 fold |
| | | | | $2.6 \times 10^2$ | |
| pBB'AD | — | 0 | 0 | $5.4 \times 10^5$ | 45 fold |
| | | | | $1.2 \times 10^4$ | |
| pBB'Atrs | — | — | 0 | 0 | — |
| | | | | 0 | |
| pAD | — | 0 | 0 | $5.2 \times 10^5$ | 47 fold |
| | | | | $1.1 \times 10^4$ | |
| pADtrs | — | — | 0 | 0 | — |
| | | | | 0 | |
| pDtrs | — | — | 0 | 0 | — |
| | | | | 0 | |
| pEGFP | — | — | 0 | 0 | — |
| | | | | 0 | |

Example 5 cis-Element Directing cAAV Replication and Packaging

Construction of Mutant cAAV Vectors. The structures of recombinant cAAV genomes are schematically presented in FIG. 1. All plasmids of this set harbor an enhanced green fluorescent protein (EGFP) under the control of the CMV promoter (Clonetech), as well as different ITR sequences derived from the TRT domain. pTRT contains an intact TRT element consisting of a single ITR flanked by two D-sequences (Duan et al. (1999) Virology 261:8-14; Musatove et al. (2000) supra). This element was derived from a CAAV clone captured using a bacterial trapping technique from cells during AAV lytic replication and appears to represent a wild-type ITR circularization point. PTRT is similar to pTRT.EG-FPori described elsewhere, but contains TRT in a flop orientation, which makes it virtually indistinguishable from a 165-bp ITR sequence in the plasmid pDD-2 previously described (Xiao et al. (1997) J. Virol. 71:941-948). The original ITR sequence of the corresponding linear vector was derived from psub201 and contains a 13-bp deletion in the A region (Samulski et al. (1987) J. Virol. 61:3096-3101). The TRT domain is identical to the ITR junction fragment found in cAAVs assembled during latent infection in vivo. All the deletion mutants were derived from this construct by replacing the TRT domain with PCR-amplified fragments containing different ITR elements. PBB'.AD has only one half of the hairpin BB' and 5 bp of the hairpin CC' followed by single A- and D-elements. pBB'.Atrs is similar to the previous construct but has the D-sequence deleted, except for the nucleotides that comprise the trs. pAD contains only A- and D-elements. patrs is a derivative of pAD, which has most of the D-element removed while leaving the trs intact. pDtrs contains a single D-sequence and part of the A-stem to complement trs. pC is a control vector that does not contain any AAV sequence. PCR was performed using high fidelity Advantage Genomic Polymerase Mix (Clonetech) and the integrity of each construct was confirmed by sequencing. All the cAAVs had the size of a wt virus and were approximately 4.4-4.6 kb in length. This permitted testing of these constructs as templates for rescue-independent packaging. Plasmids 2n (9 kb) and 3n (13.6 kb) were created by inserting respectively one or two LacZ-expressing cassettes from pCMVbeta (Clonetech) into pAD.

Models of rAAV Propagation. The first model involved co-transfection of a cis-acting plasmid with a helper plasmid expressing the adenovirus genes E2A, E4, VA RNA, and AAV Rep and Cap genes (Musatov et al. (2000) supra; Grimm et al. (1998) Hum. Gene Ther. 10:2745-2760; Collaco et al. (1999) Gene 238:397-405). The plasmids (total 2 µg DNA, 1:3 ratio) were transfected into 70-80% confluent 293 cells (which endogenously express E1A) in 35-mm culture wells using FuGene 6 (Roche). Cells were harvested 72 h post-transfection. This approach represents a helper virus-free rAAV production method.

To ensure that the findings in this study are not limited to this model, a second "classical" method for rAAV production was used as well. Subconfluent 293 cells in 35-mm culture wells were first infected with Ad5 (moi 5) for 2 h and then co-transfected with a vector plasmid and pRep.Cap (total 2 µg DNA, 1:2 ratio). The latter contains an XbaI/XbaI fragment from psub201 (33) encoding Rep and Cap proteins. Cells were harvested when advanced CPE developed, usually 48 h post-transfection.

Isolation of Hirt DNA. Cells seeded in a 35-mm culture well were harvested, washed with PBS and divided into two equal portions for extraction of extrachromosomal DNA and preparation of virus crude lysates. Low molecular weight DNA was extracted by the Hirt method (1967) J. Mol. Biol. 26:365-369, with minor modifications. Cells were resuspended in 450 µl of lysis buffer (10 mM Tris-HCl, pH 8.0, 10 mM EDTA, 100 µg/ml proteinase K) and then lysed by adding SDS (0.6% final concentration). The reaction was then incubated for 2 h at 37° C. After overnight precipitation at 4° C. with 1.1 M NaCl, cellular debris were pelleted at 16,000×g for 30 min and DNA was extracted with phenol:chloroform:isoamyl alcohol (25:24:1) and then chloroform:isoamyl alcohol (24:1). Following ethanol precipitation in the presence of glycogen (30 µg/ml final concentration, Roche), the DNA pellet was washed with 70% ethanol, dried and resuspended in 40 µl TE buffer containing DNase-free RNase (1 µg/ml final concentration, Roche).

Preparation AAV crude lysate. The other half of the cells harvested from a 35-mm dish was resuspended in 500 µl of virus lysis buffer (20 mM Tris, 150 mM NaCl). Following brief sonication the samples were subjected to one freeze-thaw cycle. After removal of cell debris by centrifugation at 3000×g for 10 min, the cleared lysates were stored at −80° C.

Analysis of AAV replication intermediates by Southern blotting. Hirt DNA (10% of total yield from a 35-mm dish) was digested in a 20-µl reaction volume with various restriction enzymes overnight. Samples were resolved on a 0.8% agarose gel, transferred to a nylon membrane (Hybond-N+, Amersham) and hybridized to a $^{32}$P-dCTP random-primer-labeled probe against the CMV.

Replication of pAD. Terminal resolution site was mutated in pAD as shown in FIG. 1 and the resulting construct pAD-mut.trs was analyzed for replication as described above. pAD was included as a positive control. Hirt DNA sample from the experiment described in FIG. 3 and above, corresponding to pAD was digested with XbaI and DpnI with or without MboI. DNA was analyzed as described above.

Replication assay for pAD plasmids of different sizes. pAD (4.4 kb), 2n (9 kb) and 3n (13.6 kb) were transfected in equimolar amounts into 293 cells together with pAd.Helper.Rep.Cap.zeo (ratio 1:3). Hirt DNA was extracted 72-h post-transfection, digested with a single-cutting enzyme plus DpnI, and separated on a 0.8% agarose gel. Given the fact that all three constructs contained different numbers of the CMV promoters (one, two or three), the blots were hybridized with a $^{32}$P-labeled probe against the unique β-lactamase fragment.

Southern blot analysis of encapsidated AAV genomes. Viral stocks of AAV.AD and AAV.TRT as a positive control (50% of total yield from a 35-mm plate) were extensively digested with DNase I, ssDNA was extracted and separated on a neutral 1% agarose gel. The blot was hybridized with a CMV promoter-specific probe.

Assay for site-specific integration. 293 cells were transfected with a Rep-expressing plasmid or pUC19 in 35-mm plates. 6 h post-transfection cells were washed and infected with AAV.TRT or AAV.AD (20% of total crude lysate from a 35-mm dish). In 12 h media was replaced and cells were incubated for an additional 60 h. Then cells were harvested and genomic DNA was extracted using Qiagen genomic DNA extraction kit.

Integration of ITR-flanked DNA in the AAVS 1 site was determined by nested PCR using primer pairs that flank the 5' or 3' end of the rAAV genome and AAVS1 site chromosome junction. Primers SM 38 (Ori, 3' end of rAAV) 5'-TAGTC-CTGTCGGGTTTCGCCAC (SEQ ID NO:8); SM 40 (CMV promoter, 5' end of rAAV) 5'-CAAGTGGGCAGTTTAC-CGTA (SEQ ID NO:9) and SM 33 (AAVS1) 5'-GCGCGCAT-AAGCCAGTAGAG (SEQ ID NO: 10) (Palombo et al. (1998) J. Virol. 72:5025-5034) were used for the first round of PCR amplification with 500 ng of genomic DNA. The reaction was performed using touchdown PCR and HotStar Taq polymerase (Qiagen). One percent of the first reaction was subjected to a second amplification using nested primers SM 20 (Ori, 3' end of rAAV) 5'-CCACCTCTGACTTGAGCGTC (SEQ ID NO: 11) or SM 39 (CMV promoter, 5' end of rAAV) 5'-TGGCGTTACTATGGGAACAT (SEQ ID NO:12) and SM 34 (AAVS1) 5'-ACAATGGCCAGGGCCAGGCAG (SEQ ID NO:13). Ten percent of the amplification product was resolved on 1.5% agarose gel in duplicates, transferred to a nylon membrane (Hybond-N+, Amersham) and hybridized to AAVS 1 or AAV ITR-specific probes. Junction fragments containing both 5' and 3' parts of rAAV genome were also subcloned into pCR2.1 (Invitrogen). Sequencing was performed by The Rockefeller University DNA sequencing laboratory using M13 forward and M13 reverse universal primers.

TABLE 4

Circular AAV replication and packaging

| Construct | Rfm and Rfd[a] | cAAV[a] | Virus yield[b] |
|---|---|---|---|
| pTRT | + | + | $2.6 \times 10^2$ |
| pBB'AD | − | + | $1.2 \times 10^4$ |
| pBB'Atrs | − | − | 0 |
| pAD | − | + | $1.1 \times 10^4$ |
| pADtrs | − | − | 0 |
| pDtrs | − | − | 0 |
| pC | − | − | 0 |

[a]As determined by Southern blot analysis.
[b]Total i.u. yield from a 35-mm plate.

TABLE 5

Packaging of pP5

| Construct | Rfm and Rfd[a] | cAAV[a] | Virus yield[b] |
|---|---|---|---|
| pP5 | − | + | $1.9 \times 10^3$ |
| pAD | − | + | $8.0 \times 10^3$ |
| pC | − | − | 0 |

[a]As determined by Southern blot analysis.
[b]Total i.u. yield from a 35-mm plate.

The invention claimed is:

1. An isolated nucleic acid sequence that directs adeno-associated virus replication exclusively in circular form, wherein the nucleotide sequence consists of SEQ ID NO: 16 or SEQ ID NO: 14.

2. The isolated nucleic acid sequence of claim 1, consisting of SEQ ID NO:16.

3. A defective circular adeno-associated virus-derived vector comprising (i) a single copy of an isolated nucleic acid sequence consisting of the nucleotides at positions 9-27 of SEQ ID NO: 16 linked 5' to a stem loop sequence consisting of a loop sequence TGGCCAA flanked on the 5' and 3' sides by complementary sequences of between 5-10 base pairs in length, wherein annealing between the complementary flanking sequences forms a hairpin structure, wherein said isolated nucleic acid sequence drives replication of said defective circular adeno-associated virus-derived vector exclusively as a circular genome and (ii) a heterologous nucleic acid sequence encoding a protein of interest, wherein said defective circular adeno-associated virus-derived vector does not comprise the nucleotides at positions 49-61 of SEQ ID NO: 16 and does not comprise a second copy of the isolated nucleic acid sequence, and replicates exclusively as a circular genome.

4. The defective circular adeno-associated virus-derived vector of claim 3, wherein the complementary flanking sequences are 7 base pairs in length.

5. The defective circular adeno-associated virus-derived vector of claim 3, wherein the complementary flanking sequences comprise a one base mismatch, resulting in improved cAAV replication.

6. The defective circular adeno-associated virus-derived vector of claim 5, wherein the complementary flanking sequences are 7 base pairs in length, and the mismatch is at base 5.

7. The vector of claim 3, wherein the heterologous nucleic acid encoding a protein of interest is operably linked to a promoter sequence.

8. The vector of claim 7, wherein the promoter is an inducible promoter.

9. The vector of claim 8, wherein the inducible promoter is selected from the group consisting of a metallothionein promoter, a tetracycline promoter, or a heat shock protein promoter.

10. The vector of claim 3, wherein the protein of interest is a therapeutic protein.

11. The vector of claim 10, wherein the therapeutic protein is insulin.

12. A defective helper vector, wherein the defective helper vector is a defective circular adeno-associated virus-derived vector that replicates exclusively as a circular genome, for use in the production of a packaged defective viral vector, wherein the defective helper vector:

(a) requires the expression and/or transcription of one or more exogenous nucleic acid(s) to replicate; and (b) comprises one or more helper heterologous nucleic acid that aids in the replication and/or packaging of a defective viral vector, and replication as a circular genome is driven by a sequence consisting of a single copy of an isolated nucleic acid sequence consisting of the nucleotides at positions 9-27 of SEQ ID NO: 16 linked 5' to a stem loop sequence consisting of a loop sequence TGGCCAA flanked on the 5' and 3' sides by complementary sequences of between 5-10 base pairs in length, wherein annealing between the complementary flanking sequences forms a hairpin structure, wherein said defective circular adeno-associated virus-derived vector does not comprise the nucleotides at positions 49-61 of SEQ ID NO: 16 and does not comprise a second copy of the isolated nucleic acid sequence.

13. The defective helper vector of claim 12, wherein the defective helper vector is a modified virus, and the modified virus is an adenovirus (Ad).

14. A composition comprising the defective helper vector of claim 13 and a defective viral vector.

15. A kit for preparing a production stock of packaged defective viral vectors (dvv) and packaged defective helper vectors (dhlpv) comprising (i) a circular adeno-associated virus (cAAV)-derived vector comprising a single copy of an isolated nucleic acid sequence consisting of the nucleotides at positions 9-27 of SEQ ID NO: 16 linked 5' to a stem loop sequence consisting of a loop sequence TGGCCAA flanked on the 5' and 3' sides by complementary sequences of between 5-10 base pairs in length, wherein annealing between the complementary flanking sequences forms a hairpin structure, wherein said defective circular adeno-associated virus-derived vector does not comprise the nucleotides at positions 49-61 of SEQ ID NO: 16 and does not comprise a second copy of the isolated nucleic acid sequence, and a nucleic acid sequence encoding a therapeutic protein of interest operably linked to a promoter sequence, wherein said isolated nucleic acid sequence drives replication of said circular adeno-associated virus-derived vector exclusively as a circular genome, and (ii) a permissive cell that comprises one or more exogenous nucleic acid(s) required to replicate and package the dhlpv, and one or more ancillary heterologous nucleic acids, the expression and/or transcription of which in conjunction with the expression and/or transcription of the helper heterologous nucleic acid(s) enables the replication and packaging of the defective viral vector in the permissive cell.

16. The kit of claim 15, further comprising a non-permissive cell lacking one or more exogenous nucleic acid(s) required to replicate and package the dhlpv, and comprising one or more ancillary heterologous nucleic acids, the expression and/or transcription of which in conjunction with the expression and/or transcription of the helper heterologous nucleic acid(s) enables the replication and packaging of the defective viral vector in the non-permissive cell.

17. A defective circular adeno-associated virus-derived vector comprising (i) a single copy of an isolated nucleic acid sequence of claim 1, wherein the isolated nucleic acid sequence is SEQ ID NO: 14 and the adeno-associated virus-derived vector does not comprise a second copy of either of the isolated nucleic acid sequences of claim 6 and does not comprise the nucleotides at positions 1-77 of SEQ ID NO: 13 and (ii) a heterologous nucleic acid sequence encoding a protein of interest, wherein said circular adeno-associated virus-derived vector replicates exclusively as a circular genome.

18. The vector of claim 17, wherein the heterologous nucleic acid encoding a protein of interest is operably linked to a promoter sequence.

19. The vector of claim 18, wherein the promoter is an inducible promoter.

20. The vector of claim 19, wherein the inducible promoter is selected from the group consisting of a metallothionein promoter, a tetracycline promoter, or a heat shock protein promoter.

21. The vector of claim 17, wherein the protein of interest is a therapeutic protein.

22. A defective helper vector, wherein the defective helper vector is a defective circular adeno-associated virus-derived vector that replicates exclusively as a circular genome, for use in the production of a packaged defective viral vector, wherein the defective helper vector:
(a) requires the expression and/or transcription of one or more exogenous nucleic acid(s) to replicate; and
(b) comprises one or more helper heterologous nucleic acid that aids in the replication and/or packaging of a defective viral vector, and a single copy of an isolated nucleic acid sequence of claim 6, wherein the isolated nucleic acid sequence is SEQ ID NO: 14, and the defective helper vector does not comprise a second copy of either of the isolated nucleic acid sequences of claim 6 and does not comprise the nucleotides at positions 1-77 of SEQ ID NO: 13 and replication as a circular genome is driven by the single copy of the isolated nucleic acid sequence of claim 1.

23. The defective helper vector of claim 22, wherein the defective helper vector is a modified virus, and the modified virus is an adenovirus (Ad).

24. A composition comprising the defective helper vector of claim 23 and a defective viral vector.

25. A kit for preparing a production stock of packaged defective viral vectors (dvv) and packaged defective helper vectors (dhlpv) comprising (i) a circular adeno-associated virus (cAAV)-derived vector comprising a single copy of an isolated nucleic acid sequence of claim 1, wherein the isolated nucleic acid sequence is SEQ ID NO: 14, and a nucleic acid sequence encoding a therapeutic protein of interest operably linked to a promoter sequence, wherein the circular adeno-associated virus-derived vector does not comprise a second copy of either of the isolated nucleic acid sequences of claim 6 and does not comprise the nucleotides at positions 1-77 of SEQ ID NO: 13, wherein the single copy of SEQ ID NO: 14 drives replication of said circular adeno-associated virus-derived vector exclusively as a circular genome, and (ii) a permissive cell that comprises one or more exogenous nucleic acid(s) required to replicate and package the dhlpv, and one or more ancillary heterologous nucleic acids, the expression and/or transcription of which in conjunction with the expression and/or transcription of the helper heterologous nucleic acid(s) enables the replication and packaging of the defective viral vector in the permissive cell.

26. The kit of claim 25, further comprising a non-permissive cell lacking one or more exogenous nucleic acid(s) required to replicate and package the dhlpv, and comprising one or more ancillary heterologous nucleic acids, the expression and/or transcription of which in conjunction with the expression and/or transcription of the helper heterologous nucleic acid(s) enables the replication and packaging of the defective viral vector in the non-permissive cell.

27. A defective circular adeno-associated virus-derived vector comprising (i) a single copy of the isolated nucleic acid sequence of claim 2, wherein the adeno-associated virus-derivedvector does not comprise a second copy of SEQ ID NO: 16 and does not comprise the nucleotides at positions 1-104 of SEQ ID NO: 13 and (ii) a heterologous nucleic acid sequence encoding a protein of interest, wherein said circular adeno-associated virus-derived vector replicates exclusively as a circular genome.

28. The vector of claim 27, wherein the heterologous nucleic acid encoding a protein of interest is operably linked to a promoter sequence.

29. The vector of claim 28, wherein the promoter is an inducible promoter.

30. The vector of claim 29, wherein the inducible promoter is selected from the group consisting of a metallothionein promoter, a tetracycline promoter, or a heat shock protein promoter.

31. The vector of claim 27, wherein the protein of interest is a therapeutic protein.

32. The vector of claim 31, wherein the therapeutic protein is insulin.

33. A defective helper vector, wherein the defective helper vector is a defective circular adeno-associated virus-derived vector that replicates exclusively as a circular genome, for use in the production of a packaged defective viral vector, wherein the defective helper vector:
(a) requires the expression and/or transcription of one or more exogenous nucleic acid(s) to replicate; and
(b) comprises one or more helper heterologous nucleic acid that aids in the replication and/or packaging of a defective viral vector, and a single copy of the isolated nucleic acid sequence of claim 2, wherein the adeno-associated virus-derived vector does not comprise a second copy of SEQ ID NO: 16 and does not comprise the nucleotides at positions 1-104 of SEQ ID NO: 13 and replication as a circular genome is driven by the single copy of SEQ ID NO: 16.

34. The defective helper vector of claim 33, wherein the defective helper vector is a modified virus, and the modified virus is an adenovirus (Ad).

35. A composition comprising the defective helper vector of claim 34 and a defective viral vector.

36. A kit for preparing a production stock of packaged defective viral vectors (dvv) and packaged defective helper vectors (dhlpv) comprising (i) a circular adeno-associated virus (cAAV)-derived vector comprising a single copy of the isolated nucleic acid sequence of claim 2 and a nucleic acid sequence encoding a therapeutic protein of interest operably linked to a promoter sequence, wherein the adeno-associated virus-derived vector does not comprise a second copy of SEQ ID NO: 16 and does not comprise the nucleotides at positions 1-104 of SEQ ID NO: 13, wherein the single copy of SEQ ID NO: 16 drives replication of said circular adeno-associated virus-derived vector exclusively as a circular genome, and (ii) a permissive cell that comprises one or more exogenous nucleic acid(s) required to replicate and package the dhlpv, and one or more ancillary heterologous nucleic acids, the expression and/or transcription of which in conjunction with the expression and/or transcription of the helper heterologous nucleic acid(s) enables the replication and packaging of the defective viral vector in the permissive cell.

37. The kit of claim 36, further comprising a non-permissive cell lacking one or more exogenous nucleic acid(s) required to replicate and package the dhlpv, and comprising one or more ancillary heterologous nucleic acids, the expression and/or transcription of which in conjunction with the expression and/or transcription of the helper heterologous nucleic acid(s) enables the replication and packaging of the defective viral vector in the non-permissive cell.

* * * * *